US009770055B2

(12) United States Patent
Cameron et al.

(10) Patent No.: US 9,770,055 B2
(45) Date of Patent: *Sep. 26, 2017

(54) VAPORIZABLE MATERIAL HANDLING FOR ELECTRONIC VAPOR DEVICE

(71) Applicant: LUNATECH, LLC, Encino, CA (US)

(72) Inventors: John Cameron, Encino, CA (US); Dean Becker, Fairhope, AL (US); Gene Fein, Oxnard, CA (US)

(73) Assignee: LUNATECH, LLC, Encino, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/155,597

(22) Filed: May 16, 2016

(65) Prior Publication Data
US 2016/0331036 A1  Nov. 17, 2016

Related U.S. Application Data

(60) Provisional application No. 62/162,546, filed on May 15, 2015.

(51) Int. Cl.
*G08C 19/16* (2006.01)
*A24F 47/00* (2006.01)
(Continued)

(52) U.S. Cl.
CPC .......... *A24F 47/008* (2013.01); *A24F 47/002* (2013.01); *A61M 11/005* (2013.01); *A61M 11/042* (2014.02); *A61M 15/0003* (2014.02); *A61M 15/009* (2013.01); *A61M 15/0021* (2014.02); *A61M 15/06* (2013.01); *G08C 17/02* (2013.01); *H04M 1/72533* (2013.01); *H04Q 9/00* (2013.01); *A61M 2016/0039* (2013.01); *A61M 2205/3368* (2013.01); *A61M 2205/3379* (2013.01); *A61M 2205/3553* (2013.01); *A61M 2205/3584* (2013.01); *A61M 2205/3592* (2013.01); *A61M 2205/3653* (2013.01); *A61M 2205/3693* (2013.01); *A61M 2205/502* (2013.01); *A61M 2205/52* (2013.01); *A61M 2205/581* (2013.01); *A61M 2205/582* (2013.01);
(Continued)

(58) Field of Classification Search
CPC ....... A24F 47/008; A24F 47/002; H04Q 9/00; A61M 15/0021; A61M 15/0003; A61M 11/005; A61M 15/009; A61M 15/06; A61M 11/042; A61M 2205/582; H04M 1/72533; F22B 1/28; G08C 17/02; G08C 2201/42
See application file for complete search history.

(56) References Cited

U.S. PATENT DOCUMENTS 7,978,564 B2 * 7/2011 De La Huerga .. A61M 5/14212
                                              221/15
8,757,147 B2   6/2014 Terry et al.
(Continued)

*Primary Examiner* — Erin File
(74) *Attorney, Agent, or Firm* — Hankin Patent Law, APC; Marc E. Hankin; Susan L. Mizer

(57) ABSTRACT

An electronic vapor device is disclosed comprising a first container for storing a vaporizable material, a vaporizer component coupled to the first container, configured for vaporizing the vaporizable material, a processor coupled to the vaporizer component, configured to control the vaporizer component in response to a disposition signal, and a network access device, coupled to the processor, configured for receiving the disposition signal from a remote server.

20 Claims, 20 Drawing Sheets

(51) Int. Cl.

| | | |
|---|---|---|
| *G08C 17/02* | (2006.01) | |
| *H04M 1/725* | (2006.01) | |
| *A61M 11/04* | (2006.01) | |
| *A61M 11/00* | (2006.01) | |
| *A61M 15/00* | (2006.01) | |
| *A61M 15/06* | (2006.01) | |
| *H04Q 9/00* | (2006.01) | |
| *A61M 16/00* | (2006.01) | |
| *F22B 1/28* | (2006.01) | |

(52) U.S. Cl.
CPC . *A61M 2205/583* (2013.01); *A61M 2205/588* (2013.01); *A61M 2205/60* (2013.01); *A61M 2205/75* (2013.01); *A61M 2205/8206* (2013.01); *F22B 1/284* (2013.01); *G08C 2201/42* (2013.01); *G08C 2201/93* (2013.01)

(56) References Cited

U.S. PATENT DOCUMENTS

| | | |
|---|---|---|
| 8,820,330 B2 | 9/2014 | Bellinger |
| 8,851,083 B2 | 10/2014 | Oglesby et al. |
| 8,955,522 B1 | 2/2015 | Bowen et al. |
| 9,408,416 B2 | 8/2016 | Monsees et al. |
| 9,498,002 B1 | 11/2016 | Soreide |
| 9,585,981 B2 | 3/2017 | Wynalda, Jr. |
| 2007/0042792 A1 | 2/2007 | Perfetto et al. |
| 2009/0255534 A1* | 10/2009 | Paterno ............ A61M 15/0028 128/203.21 |
| 2013/0298905 A1* | 11/2013 | Levin ................ A24F 47/008 128/202.21 |
| 2014/0236775 A1* | 8/2014 | Gill .................... G06Q 30/0643 705/27.2 |
| 2014/0366898 A1* | 12/2014 | Monsees ............ A24F 47/008 131/329 |
| 2015/0013695 A1 | 1/2015 | McNeal et al. |
| 2015/0027473 A1* | 1/2015 | Graf .................... F22B 1/288 131/329 |
| 2015/0136158 A1* | 5/2015 | Stevens .............. A24F 47/008 131/329 |
| 2015/0161883 A1 | 6/2015 | Satgunam |
| 2015/0181924 A1 | 7/2015 | Llamas |
| 2015/0242932 A1* | 8/2015 | Beguin ............ G06Q 30/0633 705/26.8 |
| 2015/0351449 A1 | 12/2015 | Righetti |
| 2016/0157524 A1* | 6/2016 | Bowen ............... A24F 47/008 128/200.14 |
| 2016/0198759 A1 | 7/2016 | Kuntawala |
| 2016/0286860 A1* | 10/2016 | Flayler ............... A24F 47/008 |
| 2016/0345621 A1 | 12/2016 | Li |
| 2016/0354561 A1* | 12/2016 | McCullough ...... A61M 15/0066 |
| 2016/0366928 A1 | 12/2016 | Liu |
| 2016/0371437 A1* | 12/2016 | Alarcon ............. G06Q 50/24 |
| 2017/0079322 A1 | 3/2017 | Li et al. |

* cited by examiner

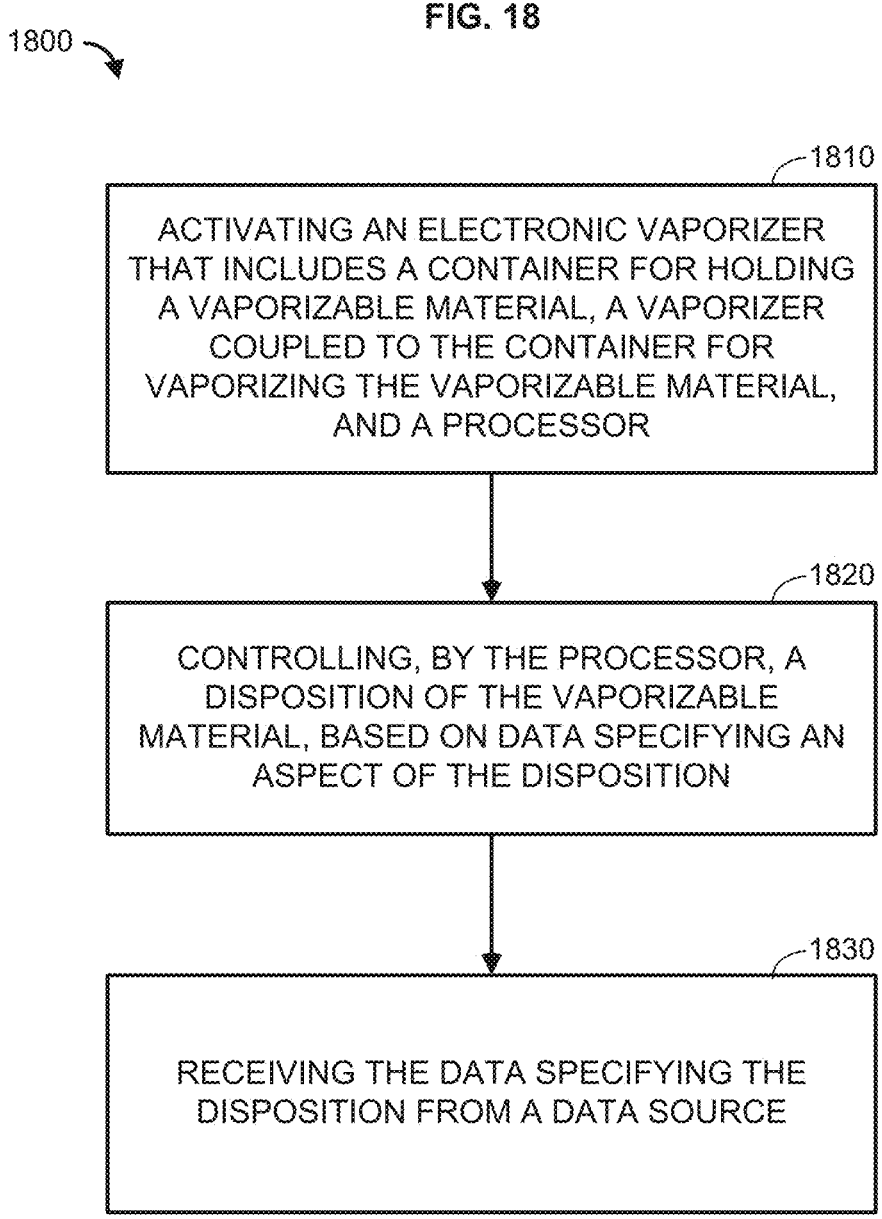

1910 — TRANSITIONING BETWEEN ENABLEMENT OF ON-DEMAND VAPORIZATION OF THE VAPORIZABLE MATERIAL AND DISABLEMENT OF SUCH VAPORIZATION

1920 — COMBINING THE VAPORIZABLE MATERIAL WITH ANOTHER VAPORIZABLE MATERIAL

1930 — COMBINING THE VAPORIZABLE MATERIAL WITH A NON-VAPORIZABLE MATERIAL

1940 — AT LEAST ONE OF TRANSFORMING THE VAPORIZABLE MATERIAL TO A DIFFERENT PHASE OR CHEMICALLY TRANSFORMING THE VAPORIZABLE MATERIAL

1950 — AT LEAST ONE OF REPLENISHING THE VAPORIZABLE MATERIAL IN THE ELECTRONIC VAPORIZER OR DEPLETING THE VAPORIZABLE MATERIAL IN THE ELECTRONIC VAPORIZER WITHOUT VAPORIZING IT

2010 — RECEIVING, BY AN ELECTRONIC VAPOR DEVICE, A DISPOSITION SIGNAL FROM A REMOTE SERVER

2020 — DETERMINING, BY THE ELECTRONIC VAPOR DEVICE, A COMMAND BASED ON THE DISPOSITION SIGNAL

2030 — EXECUTING THE COMMAND, BY THE ELECTRONIC VAPOR DEVICE, WHEREIN EXECUTING THE COMMAND AFFECTS A DISPOSITION OF A VAPORIZABLE MATERIAL

VAPORIZABLE MATERIAL HANDLING FOR ELECTRONIC VAPOR DEVICE

CROSS REFERENCE TO RELATED PATENT APPLICATION

This application claims priority to U.S. Provisional Application No. 62/162,546 filed May 15, 2015, incorporated herein by reference in its entirety.

BACKGROUND

Various types of personal vaporizers have been known in the art for many years. In general, such vaporizers are characterized by heating a solid to a smoldering point, vaporizing a liquid by heat, or nebulizing a liquid by heat and/or by expansion through a nozzle. Such devices are designed to release aromatic materials in the solid or liquid while avoiding high temperatures of combustion and associated formation of tars, carbon monoxide, or other harmful byproducts. Preferably, the device releases a very fine mist with a mouth feel similar to smoke, under suction. Thus, a vaporizing device can be made to mimic traditional smoking articles such as cigarettes, cigars, pipes and hookahs in certain aspects, while avoiding significant adverse health effects of traditional tobacco or other herbal consumption.

While various designs are long known, it is only relatively recently that technology has improved and markets have developed to the point to make mass marketing of personal vaporizers practical. A large variety of rechargeable and disposal products have become popular. In both types of popular products on the market today, control of the vaporization products is generally limited to managing the supply of a vaporizing fluid at the point of production or recharging. In other words, once a vaporizing device is supplied with its vaporizing fluid, its output is predetermined based on user control (e.g., by sucking on a mouthpiece). Accordingly, control of the output composition is not possible without replacing the vaporizing fluid or using a different device that has been supplied with a different fluid.

It would be desirable, therefore, to develop new technologies for controlling operation of a vaporizing or nebulizing device, that overcomes these and other limitations of the prior art, and enhances the utility of such devices.

SUMMARY

It is to be understood that both the following general description and the following detailed description are exemplary and explanatory only and are not restrictive. An electronic vapor device is disclosed comprising a first container for storing a vaporizable material, a vaporizer component coupled to the first container, configured for vaporizing the vaporizable material, a processor coupled to the vaporizer component, configured to control the vaporizer component in response to a disposition signal, and a network access device, coupled to the processor, configured for receiving the disposition signal from a remote server.

In an aspect, a method is disclosed comprising receiving, by an electronic vapor device, a disposition signal from a remote server, determining, by the electronic vapor device, a command based on the disposition signal, and executing the command, by the electronic vapor device, wherein executing the command affects a disposition of a vaporizable material.

Additional advantages will be set forth in part in the description which follows or can be learned by practice. The advantages will be realized and attained by means of the elements and combinations particularly pointed out in the appended claims. It is to be understood that both the foregoing general description and the following detailed description are exemplary and explanatory only and are not restrictive.

BRIEF DESCRIPTION OF THE DRAWINGS

The features, nature, and advantages of the present disclosure will become more apparent from the detailed description set forth below when taken in conjunction with the drawings, in which like reference characters are used to identify like elements correspondingly throughout the specification and drawings.

FIG. 18 illustrates an exemplary method;

FIG. 19 illustrates an exemplary method, and

FIG. 20 illustrates an exemplary method.

DETAILED DESCRIPTION

Figure 1:
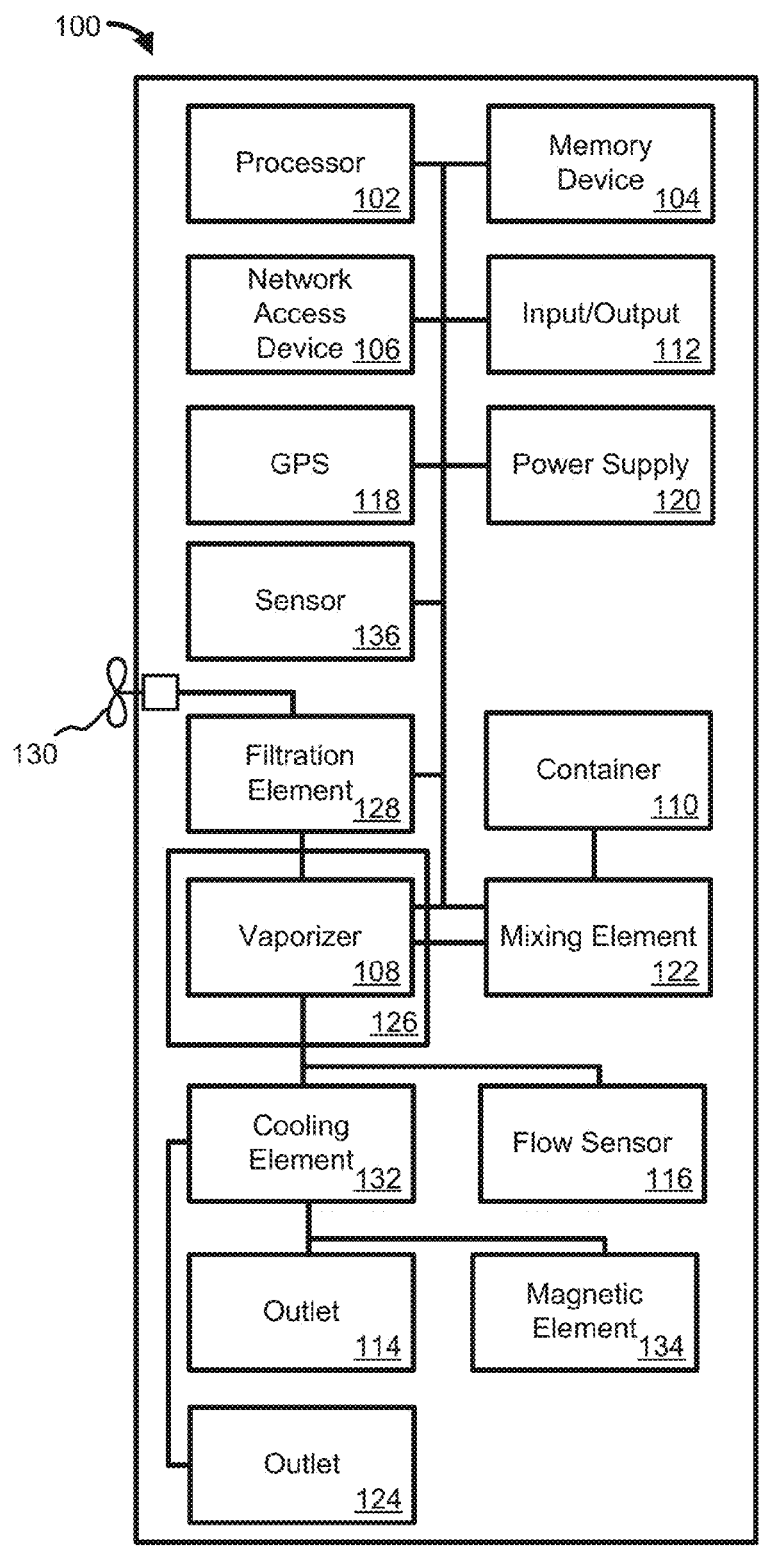
FIG. 1 illustrates a block diagram of an exemplary electronic vapor device.

Before the present methods and systems are disclosed and described, it is to be understood that the methods and systems are not limited to specific methods, specific components, or to particular implementations. It is also to be understood that the terminology used herein is for the purpose of describing particular embodiments only and is not intended to be limiting.

As used in the specification and the appended claims, the singular forms "a," "an," and "the" include plural referents unless the context clearly dictates otherwise. Ranges can be expressed herein as from "about" one particular value, and/or to "about" another particular value. When such a range is expressed, another embodiment includes¬ from the one particular value and/or to the other particular value. Similarly, when values are expressed as approximations, by use of the antecedent "about," it will be understood that the particular value forms another embodiment. It will be further understood that the endpoints of each of the ranges are significant both in relation to the other endpoint, and independently of the other endpoint.

"Optional" or "optionally" means that the subsequently described event or circumstance may or may not occur, and that the description includes instances where said event or circumstance occurs and instances where it does not.

Throughout the description and claims of this specification, the word "comprise" and variations of the word, such as "comprising" and "comprises," means "including but not limited to," and is not intended to exclude, for example, other components, integers or steps. "Exemplary" means "an example of" and is not intended to convey an indication of a preferred or ideal embodiment. "Such as" is not used in a restrictive sense, but for explanatory purposes.

Disclosed are components that can be used to perform the disclosed methods and systems. These and other components are disclosed herein, and it is understood that when combinations, subsets, interactions, groups, etc. of these components are disclosed that while specific reference of each various individual and collective combinations and permutation of these may not be explicitly disclosed, each is specifically contemplated and described herein, for all methods and systems. This applies to all aspects of this application including, but not limited to, steps in disclosed methods. Thus, if there are a variety of additional steps that can be performed it is understood that each of these additional steps can be performed with any specific embodiment or combination of embodiments of the disclosed methods.

The present methods and systems can be understood more readily by reference to the following detailed description of preferred embodiments and the examples included therein and to the Figures and their previous and following description.

As will be appreciated by one skilled in the art, the methods and systems may take the form of an entirely hardware embodiment, an entirely software embodiment, or an embodiment combining software and hardware aspects. Furthermore, the methods and systems may take the form of a computer program product on a computer-readable storage medium having computer-readable program instructions (e.g., computer software) embodied in the storage medium. More particularly, the present methods and systems may take the form of web-implemented computer software. Any suitable computer-readable storage medium can be utilized including hard disks, CD-ROMs, optical storage devices, or magnetic storage devices.

Embodiments of the methods and systems are described below with reference to block diagrams and flowchart illustrations of methods, systems, apparatuses and computer program products. It will be understood that each block of the block diagrams and flowchart illustrations, and combinations of blocks in the block diagrams and flowchart illustrations, respectively, can be implemented by computer program instructions. These computer program instructions can be loaded onto a general purpose computer, special purpose computer, or other programmable data processing apparatus to produce a machine, such that the instructions which execute on the computer or other programmable data processing apparatus create a means for implementing the functions specified in the flowchart block or blocks.

These computer program instructions may also be stored in a computer-readable memory that can direct a computer or other programmable data processing apparatus to function in a particular manner, such that the instructions stored in the computer-readable memory produce an article of manufacture including computer-readable instructions for implementing the function specified in the flowchart block or blocks. The computer program instructions may also be loaded onto a computer or other programmable data processing apparatus to cause a series of operational steps to be performed on the computer or other programmable apparatus to produce a computer-implemented process such that the instructions that execute on the computer or other programmable apparatus provide steps for implementing the functions specified in the flowchart block or blocks.

Accordingly, blocks of the block diagrams and flowchart illustrations support combinations of means for performing the specified functions, combinations of steps for performing the specified functions and program instruction means for performing the specified functions. It will also be understood that each block of the block diagrams and flowchart illustrations, and combinations of blocks in the block diagrams and flowchart illustrations, can be implemented by special purpose hardware-based computer systems that perform the specified functions or steps, or combinations of special purpose hardware and computer instructions.

Various aspects are now described with reference to the drawings. In the following description, for purposes of explanation, numerous specific details are set forth in order to provide a thorough understanding of one or more aspects. It can be evident, however, that the various aspects can be practiced without these specific details. In other instances, well-known structures and devices are shown in block diagram form in order to facilitate describing these aspects.

While embodiments of the disclosure are directed to vaporizing devices, it should be appreciated that aspects of the technology can be adapted by one of ordinary skill to nebulizing devices designed to produce an inhalable mist or aerosol.

The present disclosure relates to controlling operation of a vaporizing or nebulizing device, for example, an electronic device that uses a source of electrical power to vaporize or nebulize one or more contained materials to produce an inhalable vapor or mist.

In an aspect of the disclosure, an electronic vaporizing system, method and device include a component or process for at least one of refilling, adding deleting, blocking, transforming, mixing, removing and combining at least one vaporizable material within an electronic vapor device, facilitating greater flexibility of use scenarios for electronic vapor devices.

In an aspect, replenishment of vaporizable material may come from an at least one manually or electronically unlocked area within the device. For example, a fluid refill may be obtained from an exterior cartridge, refill station or companion device. A process in a vaporizer device wherein a vaporizable material (e.g., a fluid) may be removed, depleted or locked from access may be based on at least one of user input, signals from a control system to which the user has subscribed or from a control system operated by an authorized third party. A material may include, for example, a flavor, nutrient, vitamin, herbal essence, chemical, inert carrier, pharmaceutical or medicine)

In another aspect, protocols for at least one of the refilling, adding deleting, blocking, transforming, mixing, removing and combining at least one fluid within an electronic vapor device are determined and authorized by a remote party, for example, via a computer network. Each of these actions may be associated with a credit or debit to a user account. Such credits or debits may be tracked and recorded via an e-commerce system coupled to the computer network. E-commerce actions may be initiated manually by the user, automatically by detection of a recordable event (e.g., a refill event), archived and batch processed, determined by system settings and/or user settings.

In related aspects, the described technology may enable users to remotely access and authorize activation of a vaporization device, for example, an electronic cigarette or the like, in one or more transactions with a supplier or medical provider. The transactions may be based at least in part on measurements of vaporizable material consumed at a vaporization device identified with a specific user. The transactions may enable a user to replenish supply of a vaporizable material or unlock permission to vaporize the material at a vaporizing device. This may be useful for ordinary commercial transaction, enforcing medically-based dose regimens, or other applications.

In alternative aspects, an electronic vaporizer may include at least one of a vaporizable material coupled to an electrical circuit configured for controlling disposition of the vaporizable material and/or of the non-vaporizable material. The electronic vaporizer may include a dispenser coupled to the electric circuit for dispensing the at least one of a vaporizable material or a non-vaporizable material in at least one of an inhalable form or an ingestible form. The electrical circuit may be configured for controlling disposition of the vaporizable material prior to vaporization thereof, or after vaporization thereof. The disposition may include at least one of: transitioning between enablement of on-demand vaporization of the vaporizable material and disablement of such vaporization, blending the vaporizable material with another vaporizable material, combining the vaporizable material with the non-vaporizable material, transforming the vaporizable material or the non-vaporizable material to a different phase, chemically transforming the vaporizable material or the non-vaporizable material, replenishing the vaporizable material or the non-vaporizable material in the electronic vaporizer, depleting the vaporizable material in the electronic vaporizer without vaporizing it, or depleting the non-vaporizable material in the electronic vaporizer without dispensing it. These dispositions may be controlled locally by used input or by a predetermined control algorithm. In an alternative, or in addition, the dispositions may be controlled by input from an external source, for example a medical or therapeutic dosing service operating on a remote server.

The electronic vaporizer may exclude any non-vaporizable material (i.e., may hold only one or more vaporizable materials and not any non-vaporizable materials). Conversely, the electronic vaporizer may exclude any vaporizable material (i.e., may hold only one or more non-vaporizable materials and not any vaporizable materials). In the latter case, the vaporizer may be used temporarily or permanently as a dispenser of non-vaporizable materials in an ingestible or inhalable form.

FIG. 1 is a block diagram of an exemplary electronic vapor device 100 as described herein. The electronic vapor device 100 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vapor device 100 can comprise any suitable housing for enclosing and protecting the various components disclosed herein. The vapor device 100 can comprise a processor 102. The processor 102 can be, or can comprise, any suitable microprocessor or microcontroller, for example, a low-power application-specific controller (ASIC) and/or a field programmable gate array (FPGA) designed or programmed specifically for the task of controlling a device as described herein, or a general purpose central processing unit (CPU), for example, one based on 80×86 architecture as designed by Intel™ or AMD™, or a system-on-a-chip as designed by ARM™. The processor 102 can be coupled (e.g., communicatively, operatively, etc. . . . ) to auxiliary devices or modules of the vapor device 100 using a bus or other coupling. The vapor device 100 can comprise a power supply 110. The power supply 110 can comprise one or more batteries and/or other power storage device (e.g., capacitor) and/or a port for connecting to an external power supply. For example, an external power supply can supply power to the vapor device 100 and a battery can store at least a portion of the supplied power. The one or more batteries can be rechargeable. The one or more batteries can comprise a lithium-ion battery (including thin film lithium ion batteries), a lithium ion polymer battery, a nickel-cadmium battery, a nickel metal hydride battery, a lead-acid battery, combinations thereof, and the like. In an aspect, the power supply 110 can receive power via a power coupling to a case, wherein the vapor device 100 is stored in the case.

The vapor device 100 can comprise a memory device 104 coupled to the processor 102. The memory device 104 can comprise a random access memory (RAM) configured for storing program instructions and data for execution or processing by the processor 102 during control of the vapor device 100. When the vapor device 100 is powered off or in an inactive state, program instructions and data can be stored in a long-term memory, for example, a non-volatile magnetic optical, or electronic memory storage device (not shown). Either or both of the RAM or the long-term memory can comprise a non-transitory computer-readable medium storing program instructions that, when executed by the processor 102, cause the vapor device 100 to perform all or part of one or more methods and/or operations described herein. Program instructions can be written in any suitable high-level language, for example, C, C++, C# or the Java™, and compiled to produce machine-language code for execution by the processor 102.

In an aspect, the vapor device 100 can comprise a network access device 106 allowing the vapor device 100 to be coupled to one or more ancillary devices (not shown) such as via an access point (not shown) of a wireless telephone network, local area network, or other coupling to a wide area network, for example, the Internet. In that regard, the processor 102 can be configured to share data with the one or more ancillary devices via the network access device 106. The shared data can comprise, for example, usage data and/or operational data of the vapor device 100, a status of the vapor device 100, a status and/or operating condition of one or more the components of the vapor device 100, text to be used in a message, a product order, payment information, and/or any other data. Similarly, the processor 102 can be configured to receive control instructions from the one or more ancillary devices via the network access device 106. For example, a configuration of the vapor device 100, an operation of the vapor device 100, and/or other settings of the vapor device 100, can be controlled by the one or more ancillary devices via the network access device 106. For example, a disposition (e.g., function, operation, status, etc. . . . ) of one or more components of the vapor device 100 can be controlled via a disposition signal received via the network access device 106. The disposition signal can comprise one or more commands for disabling or enabling any component of the vapor device 100. In another aspect, the disposition signal can place the vapor device 100 in a restricted mode wherein each inhalation requires authorization from a server or an on-demand mode wherein a user can inhale vapor at will. The disposition signal can also be used, for example, to replenish one or more containers 110 with vaporizable or non-vaporizable material via an internal reservoir. In an aspect, the network access device 106 can communicate with the server to conduct a financial transaction related to the disposition signal. For example, the network access device 106 can communicate a request to refill the one or more containers 110. The server can charge a user's account for a refill and transmit a disposition signal comprising a refill command to the network access device 106 to relay to the processor 102. The processor 102 can engage a disposition control mechanism to effect the refill from the internal reservoir. Other transactions are contemplated for enabling/disabling the various components and functions of the vapor device 100.

In an aspect, the ancillary device can comprise a server that can provide one or more vaporization rates to the vapor device 100 to control the rate at which one or more vaporizable materials is vaporized. For example, an ancillary device can comprise a server that can provide various services and another ancillary device can comprise a smartphone for controlling operation of the vapor device 100. In some aspects, the smartphone or another ancillary device can be used as a primary input/output of the vapor device 100 such that data is received by the vapor device 100 from the server, transmitted to the smartphone, and output on a display of the smartphone. In an aspect, data transmitted to the ancillary device can comprise a mixture of vaporizable material and/or instructions to release vapor. For example, the vapor device 100 can be configured to determine a need for the release of vapor into the atmosphere. The vapor device 100 can provide instructions via the network access device 106 to an ancillary device (e.g., another vapor device) to release vapor into the atmosphere.

In an aspect, data can be shared anonymously. The data can be shared over a transient data session with an ancillary device. The transient data session can comprise a session limit. The session limit can be based on one or more of a number of puffs, a time limit, and a total quantity of vaporizable material. The data can comprise usage data and/or a usage profile.

In an aspect, the vapor device 100 can also comprise an input/output device 112 coupled to one or more of the processor 102, a vaporizer 108, the network access device 106, and/or any other electronic component of the vapor device 100. Input can be received from a user or another device and/or output can be provided to a user or another device via the input/output device 112. The input/output device 112 can comprise any combinations of input and/or output devices such as buttons, knobs, keyboards, touchscreens, displays, light-emitting elements, a speaker, and/or the like. In an aspect, the input/output device 112 can comprise an interface port (not shown) such as a wired interface, for example a serial port, a Universal Serial Bus (USB) port, an Ethernet port, or other suitable wired connection. The input/output device 112 can comprise a wireless interface (not shown), for example a transceiver using any suitable wireless protocol, for example WiFi (IEEE 802.11), Bluetooth®, infrared, or other wireless standard. For example, the input/output device 112 can communicate with a smartphone via Bluetooth® such that the inputs and outputs of the smartphone can be used by the user to interface with the vapor device 100. In an aspect, the input/output device 112 can comprise a user interface. The user interface user interface can comprise at least one of lighted signal lights, gauges, boxes, forms, check marks, avatars, visual images, graphic designs, lists, active calibrations or calculations, 2D interactive fractal designs, 3D fractal designs, 2D and/or 3D representations of vapor devices and other interface system functions.

In an aspect, the input/output device 112 can be coupled to an adaptor device to receive power and/or send/receive data signals from an electronic device. For example, the input/output device 112 can be configured to receive power from the adaptor device and provide the power to the power supply 120 to recharge one or more batteries. The input/output device 112 can exchange data signals received from the adaptor device with the processor 102 to cause the processor to execute one or more functions.

In an aspect, the input/output device 112 can comprise a touchscreen interface and/or a biometric interface. For example, the input/output device 112 can include controls that allow the user to interact with and input information and commands to the vapor device 100. For example, with respect to the embodiments described herein, the input/output device 112 can comprise a touch screen display. The input/output device 112 can be configured to provide the content of the exemplary screen shots shown herein, which are presented to the user via the functionality of a display. User inputs to the touch screen display are processed by, for example, the input/output device 112 and/or the processor 102. The input/output device 112 can also be configured to process new content and communications to the system 100. The touch screen display can provide controls and menu selections, and process commands and requests. Application and content objects can be provided by the touch screen display. The input/output device 112 and/or the processor 102 can receive and interpret commands and other inputs, interface with the other components of the vapor device 100 as required. In an aspect, the touch screen display can enable a user to lock, unlock, or partially unlock or lock, the vapor device 100. The vapor device 100 can be transitioned from an idle and locked state into an open state by, for example, moving or dragging an icon on the screen of the vapor device 100, entering in a password/passcode, and the like. The input/output device 112 can thus display information to a user such as a puff count, an amount of vaporizable material remaining in the container 110, battery remaining, signal strength, combinations thereof, and the like.

In an aspect, the input/output device 112 can comprise an audio user interface. A microphone can be configured to receive audio signals and relay the audio signals to the input/output device 112. The audio user interface can be any interface that is responsive to voice or other audio commands. The audio user interface can be configured to cause an action, activate a function, etc, by the vapor device 100 (or another device) based on a received voice (or other audio) command. The audio user interface can be deployed directly on the vapor device 100 and/or via other electronic devices (e.g., electronic communication devices such as a smartphone, a smart watch, a tablet, a laptop, a dedicated audio user interface device, and the like). The audio user interface can be used to control the functionality of the vapor device 100. Such functionality can comprise, but is not limited to, custom mixing of vaporizable material (e.g., eLiquids) and/or ordering custom made eLiquid combinations via an eCommerce service (e.g., specifications of a user's custom flavor mix can be transmitted to an eCommerce service, so that an eLiquid provider can mix a custom eLiquid cartridge for the user). The user can then reorder the custom flavor mix anytime or even send it to friends as a present, all via the audio user interface. The user can also send via voice command a mixing recipe to other users. The other users can utilize the mixing recipe (e.g., via an electronic vapor device having multiple chambers for eLiquid) to sample the same mix via an auto-order to the other users' devices to create the received mixing recipe. A custom mix can be given a title by a user and/or can be defined by parts (e.g., one part liquid A and two parts liquid B). The audio user interface can also be utilized to create and send a custom message to other users, to join eVapor clubs, to receive eVapor chart information, and to conduct a wide range of social networking, location services and eCommerce activities. The audio user interface can be secured via a password (e.g., audio password) which features at least one of tone recognition, other voice quality recognition and, in one aspect, can utilize at least one special cadence as part of the audio password.

The input/output device 112 can be configured to interface with other devices, for example, exercise equipment, computing equipment, communications devices and/or other vapor devices, for example, via a physical or wireless connection. The input/output device 112 can thus exchange data with the other equipment. A user may sync their vapor device 100 to other devices, via programming attributes such as mutual dynamic link library (DLL) 'hooks'. This enables a smooth exchange of data between devices, as can a web interface between devices. The input/output device 112 can be used to upload one or more profiles to the other devices. Using exercise equipment as an example, the one or more profiles can comprise data such as workout routine data (e.g., timing, distance, settings, heart rate, etc. . . . ) and vaping data (e.g., eLiquid mixture recipes, supplements, vaping timing, etc. . . . ). Data from usage of previous exercise sessions can be archived and shared with new electronic vapor devices and/or new exercise equipment so that history and preferences may remain continuous and provide for simplified device settings, default settings, and recommended settings based upon the synthesis of current and archival data.

In an aspect, the vapor device 100 can comprise a vaporizer 108. In an aspect, the vapor device 100 can comprise a plurality of vaporizers 108. The vaporizer 108 can be coupled to one or more containers 110. In an aspect, the plurality of vaporizers 108 can each be coupled to a separate container. Each of the one or more containers 110 can be configured to hold one or more vaporizable or non-vaporizable materials. The vaporizer 108 can receive the one or more vaporizable or non-vaporizable materials from the one or more containers 110 and heat the one or more vaporizable or non-vaporizable materials until the one or more vaporizable or non-vaporizable materials achieve a vapor state. In various embodiments, instead of heating the one or more vaporizable or non-vaporizable materials, the vaporizer 108 can nebulize or otherwise cause the one or more vaporizable or non-vaporizable materials in the one or more containers 110 to reduce in size into particulates. In various embodiments, the one or more containers 110 can comprise a compressed liquid that can be released to the vaporizer 108 via a valve or another mechanism. In various embodiments, the one or more containers 110 can comprise a wick (not shown) through which the one or more vaporizable or non-vaporizable materials is drawn to the vaporizer 108. The one or more containers 110 can be made of any suitable structural material, such as, an organic polymer, metal, ceramic, composite, or glass material. In an aspect, the vaporizable material can comprise one or more of, a Propylene Glycol (PG) based liquid, a Vegetable Glycerin (VG) based liquid, a water based liquid, combinations thereof, and the like. In an aspect, the vaporizable material can comprise Tetrahydrocannabinol (THC), Cannabidiol (CBD), cannabinol (CBN), combinations thereof, and the like. In a further aspect, the vaporizable material can comprise an extract from *duboisia hopwoodii*.

In an aspect, the vapor device 100 can comprise a mixing element 122. The mixing element 122 can be coupled to the processor 102 to receive one or more control signals. The one or more control signals can instruct the mixing element 122 to withdraw specific amounts of fluid from the one or more containers 110. The mixing element can, in response to a control signal from the processor 102, withdraw select quantities of vaporizable material in order to create a customized mixture of different types of vaporizable material. The liquid withdrawn by the mixing element 122 can be provided to the vaporizer 108.

The vapor device 100 may include a plurality of valves, wherein a respective one of the valves is interposed between the vaporizer 108 and a corresponding one of outlet 114 and/or outlet 124 (e.g., one or more inlets of flexible tubes). Each of the valves may control a flow rate through a respective one of the flexible tubes. For example, each of the plurality of valves may include a lumen of adjustable effective diameter for controlling a rate of vapor flow there through. The assembly may include an actuator, for example a motor, configured to independently adjust respective ones of the valves under control of the processor. The actuator may include a handle or the like to permit manual valve adjustment by the user. The motor or actuator can be coupled to a uniform flange or rotating spindle coupled to the valves and configured for controlling the flow of vapor through each of the valves. Each of the valves can be adjusted so that each of the flexible tubes accommodate the same (equal) rate of vapor flow, or different rates of flow. The processor 102 can be configured to determine settings for the respective ones of the valves each based on at least one of: a selected user preference or an amount of suction applied to a corresponding one of the flexible tubes. A user preference can be determined by the processor 102 based on a user input, which can be electrical or mechanical. An electrical input can be provided, for example, by a touchscreen, keypad, switch, or potentiometer (e.g., the input/output 112). A mechanical input can be provided, for example, by applying suction to a mouthpiece of a tube, turning a valve handle, or moving a gate piece.

The vapor device 100 may further include at least one light-emitting element positioned on or near each of the outlet 114 and/or the outlet 124 (e.g., flexible tubes) and configured to illuminate in response to suction applied to the outlet 114 and/or the outlet 124. At least one of an intensity of illumination or a pattern of alternating between an illuminated state and a non-illuminated state can be adjusted based on an amount of suction. One or more of the at least one light-emitting element, or another light-emitting element, may illuminate based on an amount of vaporizable material available. For example, at least one of an intensity of illumination or a pattern of alternating between an illuminated state and a non-illuminated state can be adjusted based on an amount of the vaporizable material within the vapor device 100. In some aspects, the vapor device 100 may include at least two light-emitting elements positioned on each of the outlet 114 and/or the outlet 124. Each of the at least two light-emitting elements may include a first light-emitting element and an outer light-emitting element positioned nearer the end of the outlet 114 and/or the outlet 124 than the first light-emitting element. Illumination of the at least two light-emitting elements may indicate a direction of a flow of vapor.

In an aspect, input from the input/output device 112 can be used by the processor 102 to cause the vaporizer 108 to vaporize the one or more vaporizable or non-vaporizable materials. For example, a user can depress a button, causing the vaporizer 108 to start vaporizing the one or more vaporizable or non-vaporizable materials. A user can then draw on an outlet 114 to inhale the vapor. In various aspects, the processor 102 can control vapor production and flow to the outlet 114 based on data detected by a flow sensor 116. For example, as a user draws on the outlet 114, the flow sensor 116 can detect the resultant pressure and provide a signal to the processor 102. In response, the processor 102 can cause the vaporizer 108 to begin vaporizing the one or more vaporizable or non-vaporizable materials, terminate vaporizing the one or more vaporizable or non-vaporizable materials, and/or otherwise adjust a rate of vaporization of the one or more vaporizable or non-vaporizable materials. The processor 102 can also determine a vaporization rate. The vaporization rate can be an amount of vaporizable material vaporized over time. In an aspect, a vaporization rate can be determined a vaporizable material. In another aspect, a vaporization rate can be determined for each of a plurality of vaporizable materials. For example, in an embodiment of the vapor device 100 comprising two different vaporizable materials, each vaporizable material can have a vaporization rate. As a result, both vaporizable materials can be vaporized at the respective vaporization rate and the resulting vapors can be combined. In another aspect, the vaporization rates can be used to determine an amount of each vaporizable material to withdraw into the mixing element 122. The resulting mixture of vaporizable material can then be vaporized. In a further aspect, each container 110 can comprise an independent vaporizer 108 configured to vaporize vaporizable material contained in a corresponding container 110 at a vaporization rate. As a result, the different vaporizable materials can be vaporized independently, yet simultaneously or serially. Vaporization can be performed according to a vaporization rate determined for each vaporizable material.

In another aspect, the vapor can exit the vapor device 100 through an outlet 124. The outlet 124 differs from the outlet 114 in that the outlet 124 can be configured to distribute the vapor into the local atmosphere, rather than being inhaled by a user. In an aspect, vapor exiting the outlet 124 can be at least one of aromatic, medicinal, recreational, and/or wellness related. In an aspect, the vapor device 100 can comprise any number of outlets. In an aspect, the outlet 114 and/or the outlet 124 can comprise at least one flexible tube. For example, a lumen of the at least one flexible tube can be in fluid communication with one or more components (e.g., a first container) of the vapor device 100 to provide vapor to a user. In more detailed aspects, the at least one flexible tube may include at least two flexible tubes. Accordingly, the vapor device 100 may further include a second container configured to receive a second vaporizable material such that a first flexible tube can receive vapor from the first vaporizable material and a second flexible tube receive vapor from the second vaporizable material. For example, the at least two flexible tubes can be in fluid communication with the first container and with second container. The vapor device 100 may include an electrical or mechanical sensor configured to sense a pressure level, and therefore suction, in an interior of the flexible tube. Application of suction may activate the vapor device 100 and cause vapor to flow.

In another aspect, the vapor device 100 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid. In an aspect, the vapor device 100 can be configured to permit a user to select between using a heating element of the vaporizer 108 or the piezoelectric dispersing element. In another aspect, the vapor device 100 can be configured to permit a user to utilize both a heating element of the vaporizer 108 and the piezoelectric dispersing element.

In an aspect, the vapor device 100 can comprise a heating casing 126. The heating casing 126 can enclose one or more of the container 110, the vaporizer 108, and/or the outlet 114. In a further aspect, the heating casing 126 can enclose one or more components that make up the container 110, the vaporizer 108, and/or the outlet 114. The heating casing 126 can be made of ceramic, metal, and/or porcelain. The heating casing 126 can have varying thickness. In an aspect, the heating casing 126 can be coupled to the power supply 120 to receive power to heat the heating casing 126. In another aspect, the heating casing 126 can be coupled to the vaporizer 108 to heat the heating casing 126. In another aspect, the heating casing 126 can serve an insulation role.

In an aspect, the vapor device 100 can comprise a filtration element 128. The filtration element 128 can be configured to remove (e.g., filter, purify, etc) contaminants from air entering the vapor device 100. The filtration element 128 can optionally comprise a fan 130 to assist in delivering air to the filtration element 128. The vapor device 100 can be configured to intake air into the filtration element 128, filter the air, and pass the filtered air to the vaporizer 108 for use in vaporizing the one or more vaporizable or non-vaporizable materials. In another aspect, the vapor device 100 can be configured to intake air into the filtration element 128, filter the air, and bypass the vaporizer 108 by passing the filtered air directly to the outlet 114 for inhalation by a user.

In an aspect, the filtration element 128 can comprise cotton, polymer, wool, satin, meta materials and the like. The filtration element 128 can comprise a filter material that at least one airborne particle and/or undesired gas by a mechanical mechanism, an electrical mechanism, and/or a chemical mechanism. The filter material can comprise one or more pieces of a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 128 can comprise electrostatic plates, ultraviolet light, a HEPA filter, combinations thereof, and the like.

In an aspect, the vapor device 100 can comprise a cooling element 132. The cooling element 132 can be configured to cool vapor exiting the vaporizer 108 prior to passing through the outlet 114. The cooling element 132 can cool vapor by utilizing air or space within the vapor device 100. The air used by the cooling element 132 can be either static (existing in the vapor device 100) or drawn into an intake and through the cooling element 132 and the vapor device 100. The intake can comprise various pumping, pressure, fan, or other intake systems for drawing air into the cooling element 132. In an aspect, the cooling element 132 can reside separately or can be integrated the vaporizer 108. The cooling element 132 can be a single cooled electronic element within a tube or space and/or the cooling element 132 can be configured as a series of coils or as a grid like structure. The materials for the cooling element 132 can be metal, liquid, polymer, natural substance, synthetic substance, air, or any combination thereof. The cooling element 132 can be powered by the power supply 120, by a separate battery (not shown), or other power source (not shown) including the use of excess heat energy created by the vaporizer 108 being converted to energy used for cooling by virtue of a small turbine or pressure system to convert the energy. Heat differentials between the vaporizer 108 and the cooling element 132 can also be converted to energy utilizing commonly known geothermal energy principles.

In an aspect, the vapor device 100 can comprise a magnetic element 134. For example, the magnetic element 134 can comprise an electromagnet, a ceramic magnet, a ferrite magnet, and/or the like. The magnetic element 134 can be configured to apply a magnetic field to air as it is brought into the vapor device 100, in the vaporizer 108, and/or as vapor exits the outlet 114.

The input/output device 112 can be used to select whether vapor exiting the outlet 114 should be cooled or not cooled and/or heated or not heated and/or magnetized or not magnetized. For example, a user can use the input/output device 112 to selectively cool vapor at times and not cool vapor at other times. The user can use the input/output device 112 to selectively heat vapor at times and not heat vapor at other times. The user can use the input/output device 112 to selectively magnetize vapor at times and not magnetize vapor at other times. The user can further use the input/output device 112 to select a desired smoothness, temperature, and/or range of temperatures. The user can adjust the temperature of the vapor by selecting or clicking on a clickable setting on a part of the vapor device 100. The user can use, for example, a graphical user interface (GUI) or a mechanical input enabled by virtue of clicking a rotational mechanism at either end of the vapor device 100.

In an aspect, cooling control can be set within the vapor device 100 settings via the processor 102 and system software (e.g., dynamic linked libraries). The memory 104 can store settings. Suggestions and remote settings can be communicated to and/or from the vapor device 100 via the input/output device 112 and/or the network access device 106. Cooling of the vapor can be set and calibrated between heating and cooling mechanisms to what is deemed an ideal temperature by the manufacturer of the vapor device 100 for the vaporizable material. For example, a temperature can be set such that resultant vapor delivers the coolest feeling to the average user but does not present any health risk to the user by virtue of the vapor being too cold, including the potential for rapid expansion of cooled vapor within the lungs and the damaging of tissue by vapor which has been cooled to a temperature which may cause frostbite like symptoms.

In an aspect, the vapor device 100 can be configured to receive air, smoke, vapor or other material and analyze the contents of the air, smoke, vapor or other material using one or more sensors 136 in order to at least one of analyze, classify, compare, validate, refute, and/or catalogue the same. A result of the analysis can be, for example, an identification of at least one of medical, recreational, homeopathic, olfactory elements, spices, other cooking ingredients, ingredients analysis from food products, fuel analysis, pharmaceutical analysis, genetic modification testing analysis, dating, fossil and/or relic analysis and the like. The vapor device 100 can pass utilize, for example, mass spectrometry, PH testing, genetic testing, particle and/or cellular testing, sensor based testing and other diagnostic and wellness testing either via locally available components or by transmitting data to a remote system for analysis.

In an aspect, a user can create a custom scent by using the vapor device 100 to intake air elements, where the vapor device 100 (or third-party networked device) analyzes the olfactory elements and/or biological elements within the sample and then formulates a replica scent within the vapor device 100 (or third-party networked device) that can be accessed by the user instantly, at a later date, with the ability to purchase this custom scent from a networked ecommerce portal.

In another aspect, the one or more sensors 136 can be configured to sense negative environmental conditions (e.g., adverse weather, smoke, fire, chemicals (e.g., such as $CO_2$ or formaldehyde), adverse pollution, and/or disease outbreaks, and the like). The one or more sensors 136 can comprise one or more of, a biochemical/chemical sensor, a thermal sensor, a radiation sensor, a mechanical sensor, an optical sensor, a mechanical sensor, a magnetic sensor, an electrical sensor, combinations thereof and the like. The biochemical/chemical sensor can be configured to detect one or more biochemical/chemicals causing a negative environmental condition such as, but not limited to, smoke, a vapor, a gas, a liquid, a solid, an odor, combinations thereof, and/or the like. The biochemical/chemical sensor can comprise one or more of a mass spectrometer, a conducting/nonconducting regions sensor, a SAW sensor, a quartz microbalance sensor, a conductive composite sensor, a chemiresitor, a metal oxide gas sensor, an organic gas sensor, a MOSFET, a piezoelectric device, an infrared sensor, a sintered metal oxide sensor, a Pd-gate MOSFET, a metal FET structure, a electrochemical cell, a conducting polymer sensor, a catalytic gas sensor, an organic semiconducting gas sensor, a solid electrolyte gas sensors, a piezoelectric quartz crystal sensor, and/or combinations thereof.

The thermal sensor can be configured to detect temperature, heat, heat flow, entropy, heat capacity, combinations thereof, and the like. Exemplary thermal sensors include, but are not limited to, thermocouples, such as a semiconducting thermocouples, noise thermometry, thermoswitches, thermistors, metal thermoresistors, semiconducting thermoresistors, thermodiodes, thermotransistors, calorimeters, thermometers, indicators, and fiber optics.

The radiation sensor can be configured to detect gamma rays, X-rays, ultra-violet rays, visible, infrared, microwaves and radio waves. Exemplary radiation sensors include, but are not limited to, nuclear radiation microsensors, such as scintillation counters and solid state detectors, ultra-violet, visible and near infrared radiation microsensors, such as photoconductive cells, photodiodes, phototransistors, infrared radiation microsensors, such as photoconductive IR sensors and pyroelectric sensors.

The optical sensor can be configured to detect visible, near infrared, and infrared waves. The mechanical sensor can be configured to detect displacement, velocity, acceleration, force, torque, pressure, mass, flow, acoustic wavelength, and amplitude. Exemplary mechanical sensors include, but are not limited to, displacement microsensors, capacitive and inductive displacement sensors, optical displacement sensors, ultrasonic displacement sensors, pyroelectric, velocity and flow microsensors, transistor flow microsensors, acceleration microsensors, piezoresistive microaccelerometers, force, pressure and strain microsensors, and piezoelectric crystal sensors. The magnetic sensor can be configured to detect magnetic field, flux, magnetic moment, magnetization, and magnetic permeability. The electrical sensor can be configured to detect charge, current, voltage, resistance, conductance, capacitance, inductance, dielectric permittivity, polarization and frequency.

Upon sensing a negative environmental condition, the one or more sensors 122 can provide data to the processor 102 to determine the nature of the negative environmental condition and to generate/transmit one or more alerts based on the negative environmental condition. The one or more alerts can be deployed to the vapor device 100 user's wireless device and/or synced accounts. For example, the network device access device 106 can be used to transmit the one or more alerts directly (e.g., via Bluetooth®) to a user's smartphone to provide information to the user. In another aspect, the network access device 106 can be used to transmit sensed information and/or the one or more alerts to a remote server for use in syncing one or more other devices used by the user (e.g., other vapor devices, other electronic devices (smartphones, tablets, laptops, etc. . . . ). In another aspect, the one or more alerts can be provided to the user of the vapor device 100 via vibrations, audio, colors, and the like deployed from the mask, for example through the input/output device 112. For example, the input/output device 112 can comprise a small vibrating motor to alert the user to one or more sensed conditions via tactile sensation. In another example, the input/output device 112 can comprise one or more LED's of various colors to provide visual information to the user. In another example, the input/output device 112 can comprise one or more speakers that can provide audio information to the user. For example, various patterns of beeps, sounds, and/or voice recordings can be utilized to provide the audio information to the user. In another example, the input/output device 112 can comprise an LCD screen/touchscreen that provides a summary and/or detailed information regarding the negative environmental condition and/or the one or more alerts.

In another aspect, upon sensing a negative environmental condition, the one or more sensors 136 can provide data to the processor 102 to determine the nature of the negative environmental condition and to provide a recommendation for mitigating and/or to actively mitigate the negative environmental condition. Mitigating the negative environmental conditions can comprise, for example, applying a filtration system, a fan, a fire suppression system, engaging a HVAC system, and/or one or more vaporizable and/or non-vaporizable materials. The processor 102 can access a database stored in the memory device 104 to make such a determination or the network device 106 can be used to request information from a server to verify the sensor findings. In an aspect, the server can provide an analysis service to the vapor device 100. For example, the server can analyze data sent by the vapor device 100 based on a reading from the one or more sensors 136. The server can determine and transmit one or more recommendations to the vapor device 100 to mitigate the sensed negative environmental condition. The vapor device 100 can use the one or more recommendations to activate a filtration system, a fan, a fire suppression system engaging a HVAC system, and/or to vaporize one or more vaporizable or non-vaporizable materials to assist in countering effects from the negative environmental condition.

In an aspect, the vapor device 100 can comprise a global positioning system (GPS) unit 118. The GPS 118 can detect a current location of the device 100. In some aspects, a user can request access to one or more services that rely on a current location of the user. For example, the processor 102 can receive location data from the GPS 118, convert it to usable data, and transmit the usable data to the one or more services via the network access device 106. GPS unit 118 can receive position information from a constellation of satellites operated by the U.S. Department of Defense. Alternately, the GPS unit 118 can be a GLONASS receiver operated by the Russian Federation Ministry of Defense, or any other positioning device capable of providing accurate location information (for example, LORAN, inertial navigation, and the like). The GPS unit 118 can contain additional logic, either software, hardware or both to receive the Wide Area Augmentation System (WAAS) signals, operated by the Federal Aviation Administration, to correct dithering errors and provide the most accurate location possible. Overall accuracy of the positioning equipment subsystem containing WAAS is generally in the two meter range.

Figure 2:
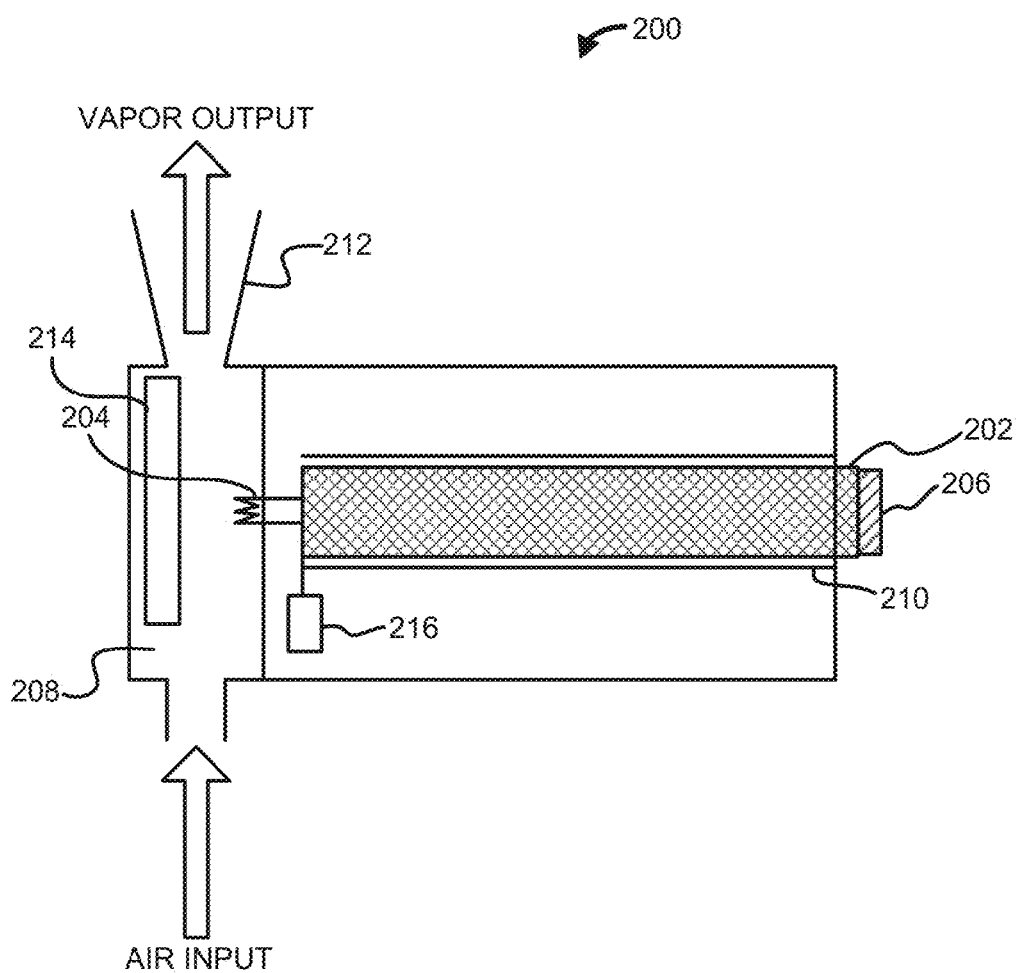
FIG. 2 illustrates an exemplary vaporizer.

FIG. 2 illustrates an exemplary vaporizer 200. The vaporizer 200 can be, for example, an e-cigarette, an e-cigar, an electronic vapor device, a hybrid electronic communication handset coupled/integrated vapor device, a robotic vapor device, a modified vapor device "mod," a micro-sized electronic vapor device, a robotic vapor device, and the like. The vaporizer 200 can be used internally of the vapor device 100 or can be a separate device. For example, the vaporizer 200 can be used in place of the vaporizer 108.

The vaporizer 200 can comprise or be coupled to one or more containers 202 containing a vaporizable material, for example a fluid. For example, coupling between the vaporizer 200 and the one or more containers 202 can be via a wick 204, via a valve, or by some other structure. Coupling can operate independently of gravity, such as by capillary action or pressure drop through a valve. The vaporizer 200 can be configured to vaporize the vaporizable material from the one or more containers 202 at controlled rates in response to mechanical input from a component of the vapor device 100, and/or in response to control signals from the processor 102 or another component. Vaporizable material (e.g., fluid) can be supplied by one or more replaceable cartridges 206. In an aspect the vaporizable material can comprise aromatic elements. In an aspect, the aromatic elements can be medicinal, recreational, and/or wellness related. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). The one or more replaceable cartridges 206 can contain the vaporizable material. If the vaporizable material is liquid, the cartridge can comprise the wick 204 to aid in transporting the liquid to a mixing chamber 208. In the alternative, some other transport mode can be used. Each of the one or more replaceable cartridges 206 can be configured to fit inside and engage removably with a receptacle (such as the container 202 and/or a secondary container) of the vapor device 100. In an alternative, or in addition, one or more fluid containers 210 can be fixed in the vapor device 100 and configured to be refillable. In an aspect, one or more materials can be vaporized at a single time by the vaporizer 200. For example, some material can be vaporized and drawn through an exhaust port 212 and/or some material can be vaporized and exhausted via a smoke simulator outlet (not shown).

The mixing chamber 208 can also receive an amount of one or more compounds (e.g., vaporizable material) to be vaporized. For example, the processor 102 can determine a first amount of a first compound and determine a second amount of a second compound. The processor 102 can cause the withdrawal of the first amount of the first compound from a first container into the mixing chamber and the second amount of the second compound from a second container into the mixing chamber. The processor 102 can also determine a target dose of the first compound, determine a vaporization ratio of the first compound and the second compound based on the target dose, determine the first amount of the first compound based on the vaporization ratio, determine the second amount of the second compound based on the vaporization ratio, and cause the withdrawal of the first amount of the first compound into the mixing chamber, and the withdrawal of the second amount of the second compound into the mixing chamber.

The processor 102 can also determine a vaporization rate. The vaporization rate can be an amount of vaporizable material vaporized over time. In an aspect, a vaporization rate can be determined a vaporizable material. In another aspect, a vaporization rate can be determined for each of a plurality of vaporizable materials. For example, in an embodiment of the vapor device 100 comprising two different vaporizable materials, each vaporizable material can have a vaporization rate. As a result, both vaporizable materials can be vaporized at the respective vaporization rate and the resulting vapors can be combined. In another aspect, the vaporization rates can be used to determine an amount of each vaporizable material to withdraw into the mixing element 122. The resulting mixture of vaporizable material can then be vaporized. In a further aspect, each container 110 can comprise an independent vaporizer 108 configured to vaporize vaporizable material contained in a corresponding container at a vaporization rate. As a result, the different vaporizable materials can be vaporized independently, yet simultaneously or serially. Vaporization can be performed according to a vaporization rate determined for each vaporizable material.

The processor 102 can also determine a target dose of the first compound, determine a vaporization ratio of the first compound and the second compound based on the target dose, determine the first amount of the first compound based on the vaporization ratio, and determine the second amount of the second compound based on the vaporization ratio. After expelling the vapor through an exhaust port for inhalation by a user, the processor 102 can determine that a cumulative dose is approaching the target dose and reduce the vaporization ratio. In an aspect, one or more of the vaporization ratio, the target dose, and/or the cumulative dose can be determined remotely and transmitted to the vapor device 100 for use.

In operation, a heating element 214 can vaporize or nebulize the vaporizable material in the mixing chamber 208, producing an inhalable vapor/mist that can be expelled via the exhaust port 212. In an aspect, the vaporizer 200 can comprise a plurality of heating elements 214 configured to independently heat different vaporizable materials. In an aspect, the heating element 214 can comprise a heater coupled to the wick (or a heated wick) 204 operatively coupled to (for example, in fluid communication with) the mixing chamber 210. The heating element 214 can comprise a nickel-chromium wire or the like, with a temperature sensor (not shown) such as a thermistor or thermocouple. Within definable limits, by controlling power to the wick 204, a rate of vaporization can be independently controlled. A multiplexer 216 can receive power from any suitable source and exchange data signals with a processor, for example, the processor 102 of the vapor device 100, for control of the vaporizer 200. At a minimum, control can be provided between no power (off state) and one or more powered states. Other control mechanisms can also be suitable.

In another aspect, the vaporizer 200 can comprise a piezoelectric dispersing element. In some aspects, the piezoelectric dispersing element can be charged by a battery, and can be driven by a processor on a circuit board. The circuit board can be produced using a polyimide such as Kapton, or other suitable material. The piezoelectric dispersing element can comprise a thin metal disc which causes dispersion of the fluid fed into the dispersing element via the wick or other soaked piece of organic material through vibration. Once in contact with the piezoelectric dispersing element, the vaporizable material (e.g., fluid) can be vaporized (e.g., turned into vapor or mist) and the vapor can be dispersed via a system pump and/or a sucking action of the user. In some aspects, the piezoelectric dispersing element can cause dispersion of the vaporizable material by producing ultrasonic vibrations. An electric field applied to a piezoelectric material within the piezoelectric element can cause ultrasonic expansion and contraction of the piezoelectric material, resulting in ultrasonic vibrations to the disc. The ultrasonic vibrations can cause the vaporizable material to disperse, thus forming a vapor or mist from the vaporizable material.

In an aspect, the vaporizer 200 can be configured to permit a user to select between using the heating element 214 or the piezoelectric dispersing element. In another aspect, the vaporizer 200 can be configured to permit a user to utilize both the heating element 214 and the piezoelectric dispersing element.

In some aspects, the connection between a power supply and the piezoelectric dispersing element can be facilitated using one or more conductive coils. The conductive coils can provide an ultrasonic power input to the piezoelectric dispersing element. For example, the signal carried by the coil can have a frequency of approximately 107.8 kHz. In some aspects, the piezoelectric dispersing element can comprise a piezoelectric dispersing element that can receive the ultrasonic signal transmitted from the power supply through the coils, and can cause vaporization of the vaporizable liquid by producing ultrasonic vibrations. An ultrasonic electric field applied to a piezoelectric material within the piezoelectric element causes ultrasonic expansion and contraction of the piezoelectric material, resulting in ultrasonic vibrations according to the frequency of the signal. The vaporizable liquid can be vibrated by the ultrasonic energy produced by the piezoelectric dispersing element, thus causing dispersal and/or atomization of the liquid.

Figure 3:
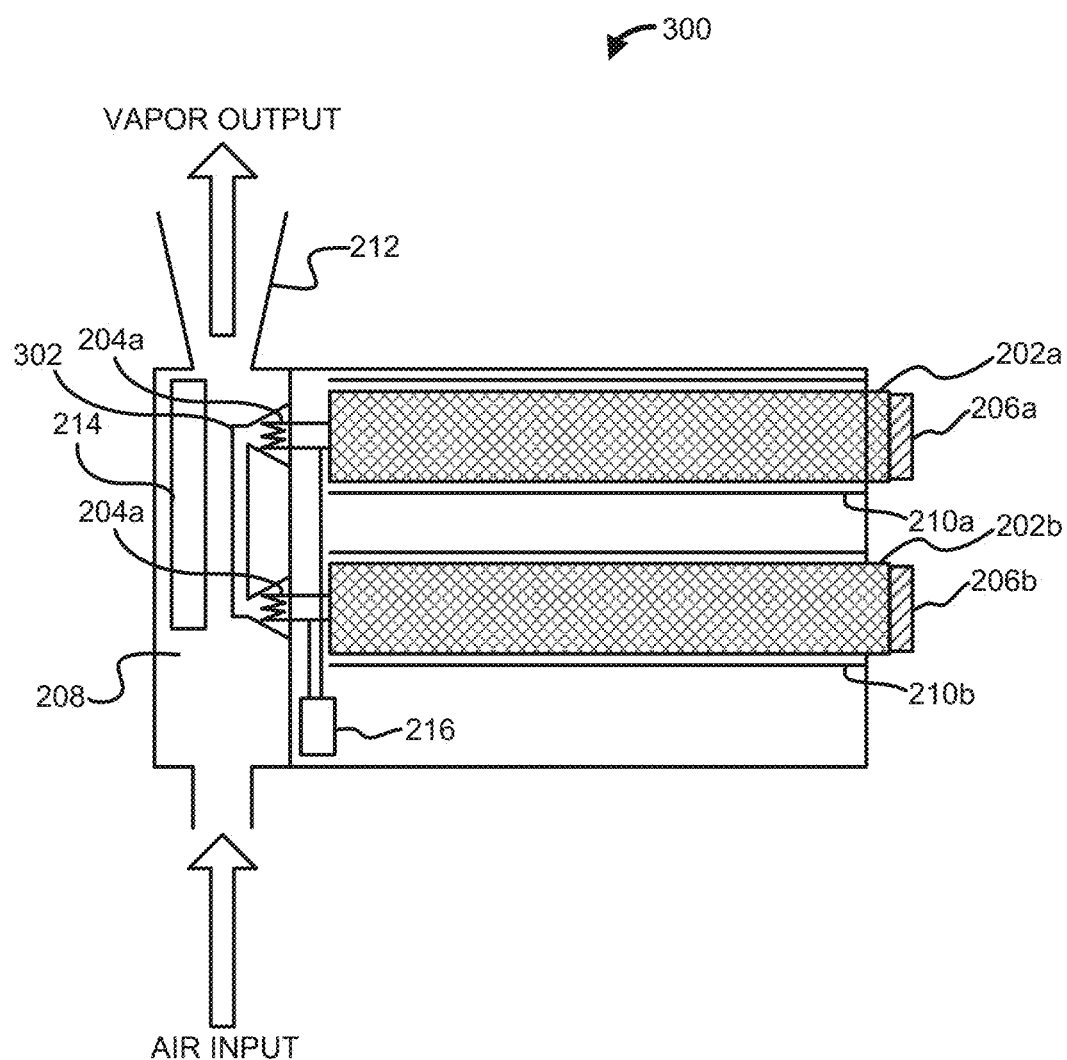
FIG. 3 illustrates an exemplary vaporizer configured for vaporizing a mixture of vaporizable material.

FIG. 3 illustrates a vaporizer 300 that comprises the elements of the vaporizer 200 with two containers 202a and 202b containing a vaporizable material, for example a fluid or a solid. In an aspect, the fluid can be the same fluid in both containers or the fluid can be different in each container. In an aspect the fluid can comprise aromatic elements. The aromatic element can include, but is not limited to, at least one of lavender or other floral aromatic eLiquids, mint, menthol, herbal soil or geologic, plant based, name brand perfumes, custom mixed perfume formulated inside the vapor device 100 and aromas constructed to replicate the smell of different geographic places, conditions, and/or occurrences. For example, the smell of places may include specific or general sports venues, well known travel destinations, the mix of one's own personal space or home. The smell of conditions may include, for example, the smell of a pet, a baby, a season, a general environment (e.g., a forest), a new car, a sexual nature (e.g., musk, pheromones, etc. . . . ). Coupling between the vaporizer 200 and the container 202a and the container 202b can be via a wick 204a and a wick 204b, respectively, via a valve, or by some other structure. Coupling can operate independently of gravity, such as by capillary action or pressure drop through a valve. The vaporizer 300 can be configured to mix in varying proportions the fluids contained in the container 202a and the container 202b and vaporize the mixture at controlled rates in response to mechanical input from a component of the vapor device 100, and/or in response to control signals from the processor 102 or another component. For example, based on a vaporization ratio. In an aspect, a mixing element 302 can be coupled to the container 202a and the container 202b. The mixing element can, in response to a control signal from the processor 102, withdraw select quantities of vaporizable material in order to create a customized mixture of different types of vaporizable material. Vaporizable material (e.g., fluid) can be supplied by one or more replaceable cartridges 206a and 206b. The one or more replaceable cartridges 206a and 206b can contain a vaporizable material. If the vaporizable material is liquid, the cartridge can comprise the wick 204a or 204b to aid in transporting the liquid to a mixing chamber 208. In the alternative, some other transport mode can be used. Each of the one or more replaceable cartridges 206a and 206b can be configured to fit inside and engage removably with a receptacle (such as the container 202a or the container 202b and/or a secondary container) of the vapor device 100. In an alternative, or in addition, one or more fluid containers 210a and 210b can be fixed in the vapor device 100 and configured to be refillable. In an aspect, one or more materials can be vaporized at a single time by the vaporizer 300. For example, some material can be vaporized and drawn through an exhaust port 212 and/or some material can be vaporized and exhausted via a smoke simulator outlet (not shown).

Figure 4:
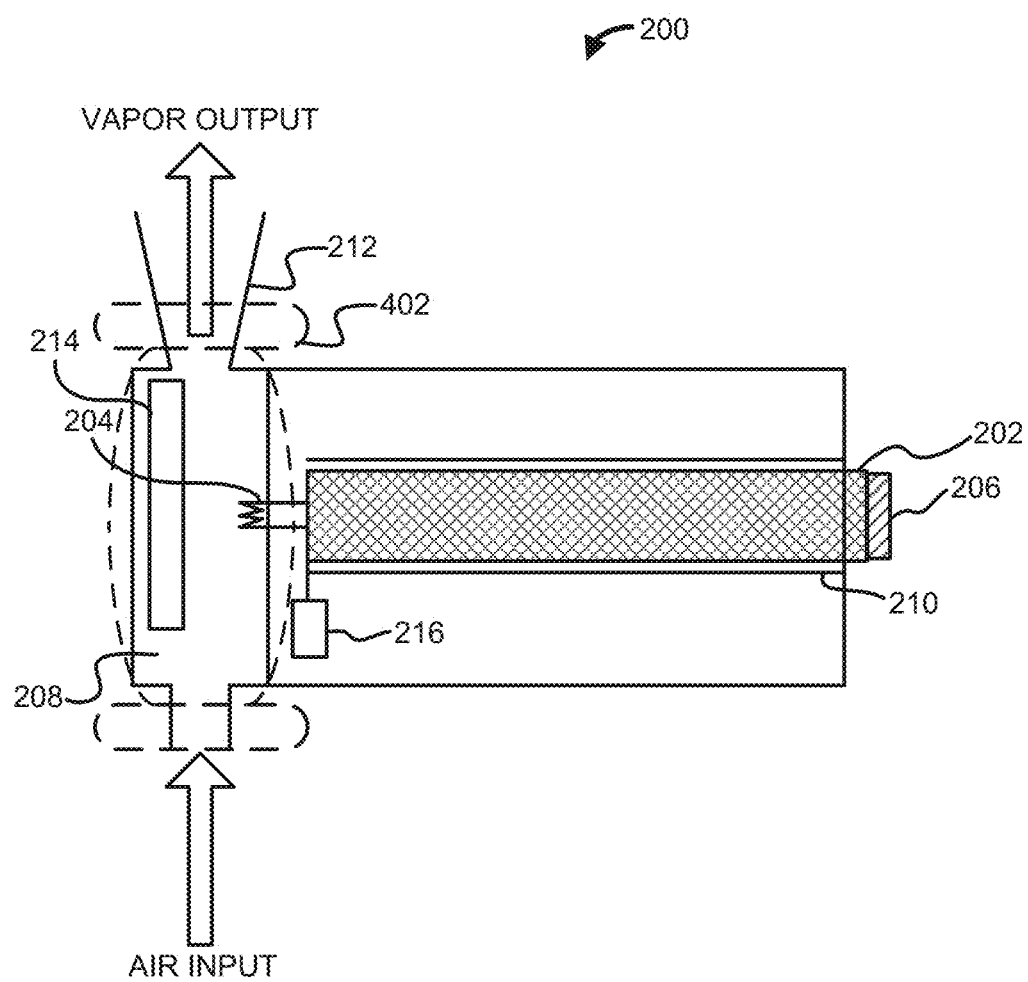
FIG. 4 illustrates an exemplary vaporizer device configured for smooth vapor delivery.

FIG. 4 illustrates a vaporizer 200 that comprises the elements of the vaporizer 200 with a heating casing 402. The heating casing 402 can enclose the heating element 214 or can be adjacent to the heating element 214. The heating casing 402 is illustrated with dashed lines, indicating components contained therein. The heating casing 402 can be made of ceramic, metal, and/or porcelain. The heating casing 402 can have varying thickness. In an aspect, the heating casing 402 can be coupled to the multiplexer 216 to receive power to heat the heating casing 402. In another aspect, the heating casing 402 can be coupled to the heating element 214 to heat the heating casing 402. In another aspect, the heating casing 402 can serve an insulation role.

Figure 5:
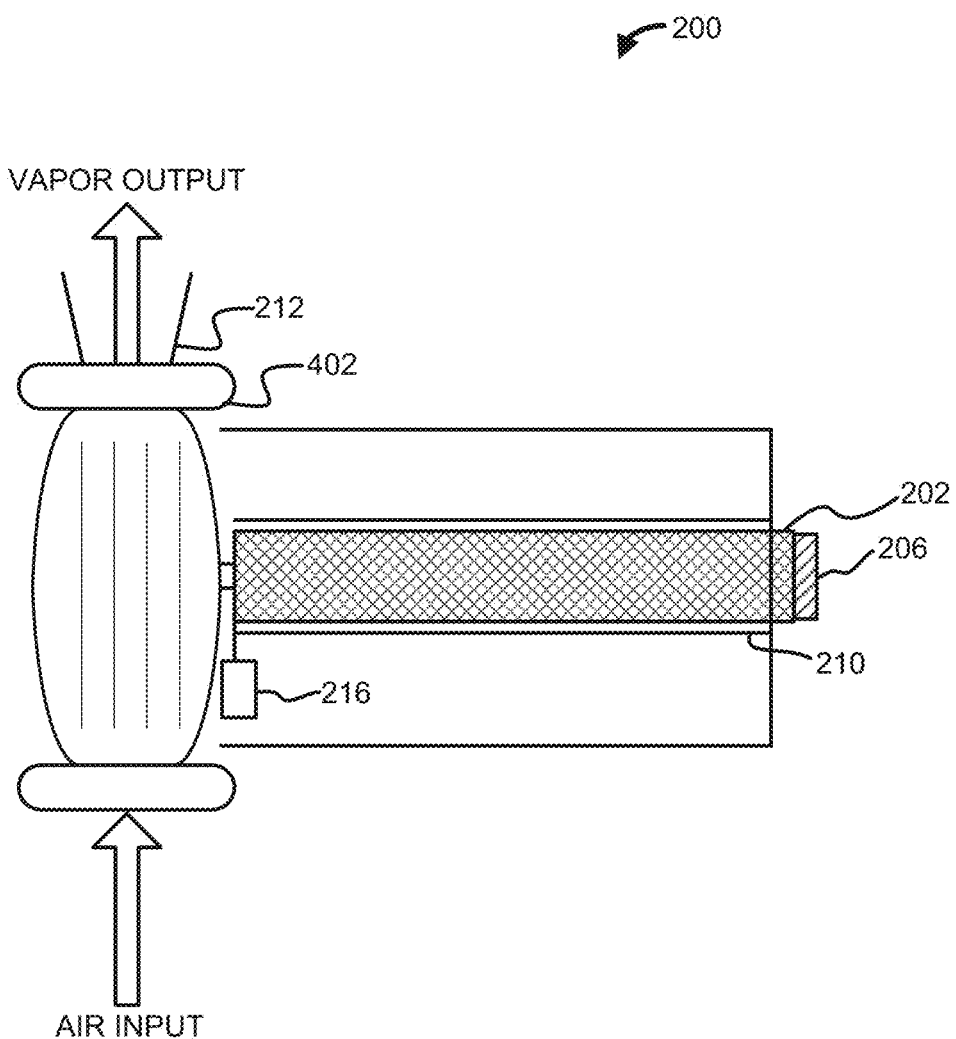
FIG. 5 illustrates another exemplary vaporizer configured for smooth vapor delivery.

FIG. 5 illustrates the vaporizer 200 of FIG. 2 and FIG. 4, but illustrates the heating casing 402 with solid lines, indicating components contained therein. Other placements of the heating casing 402 are contemplated. For example, the heating casing 402 can be placed after the heating element 214 and/or the mixing chamber 208.

Figure 6:
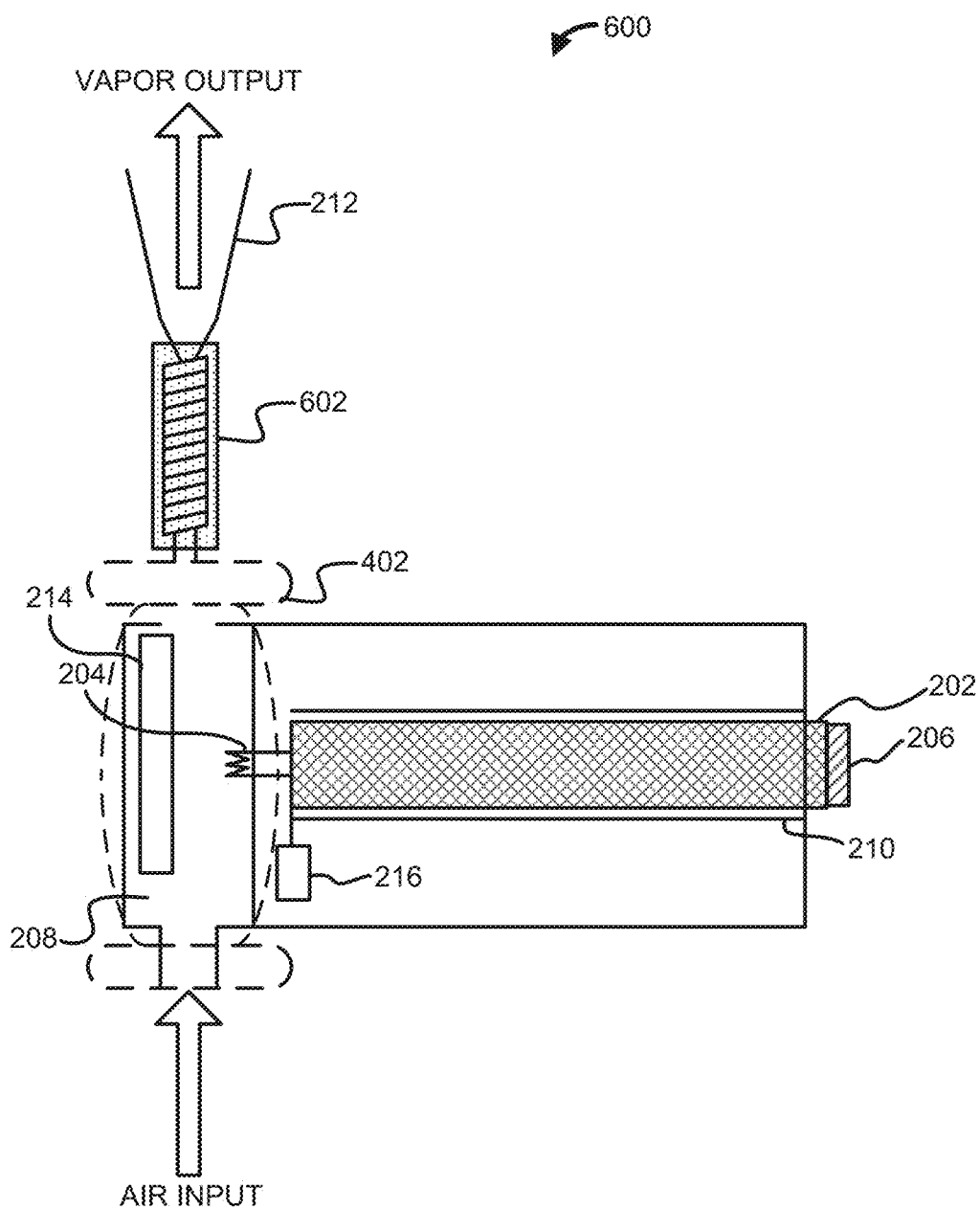
FIG. 6 illustrates another exemplary vaporizer configured for smooth vapor delivery.

FIG. 6 illustrates a vaporizer 600 that comprises the elements of the vaporizer 200 of FIG. 2 and FIG. 4, with the addition of a cooling element 602. The vaporizer 600 can optionally comprise the heating casing 402. The cooling element 602 can comprise one or more of a powered cooling element, a cooling air system, and/or or a cooling fluid system. The cooling element 602 can be self-powered, co-powered, or directly powered by a battery and/or charging system within the vapor device 100 (e.g., the power supply 120). In an aspect, the cooling element 602 can comprise an electrically connected conductive coil, grating, and/or other design to efficiently distribute cooling to the at least one of the vaporized and/or non-vaporized air. For example, the cooling element 602 can be configured to cool air as it is brought into the vaporizer 600/mixing chamber 208 and/or to cool vapor after it exits the mixing chamber 208. The cooling element 602 can be deployed such that the cooling element 602 is surrounded by the heated casing 402 and/or the heating element 214. In another aspect, the heated casing 402 and/or the heating element 214 can be surrounded by the cooling element 602. The cooling element 602 can utilize at least one of cooled air, cooled liquid, and/or cooled matter.

In an aspect, the cooling element 602 can be a coil of any suitable length and can reside proximate to the inhalation point of the vapor (e.g., the exhaust port 212). The temperature of the air is reduced as it travels through the cooling element 602. In an aspect, the cooling element 602 can comprise any structure that accomplishes a cooling effect. For example, the cooling element 602 can be replaced with a screen with a mesh or grid-like structure, a conical structure, and/or a series of cooling airlocks, either stationary or opening, in a periscopic/telescopic manner. The cooling element 602 can be any shape and/or can take multiple forms capable of cooling heated air, which passes through its space.

In an aspect, the cooling element 602 can be any suitable cooling system for use in a vapor device. For example, a fan, a heat sink, a liquid cooling system, a chemical cooling system, combinations thereof, and the like. In an aspect, the cooling element 602 can comprise a liquid cooling system whereby a fluid (e.g., water) passes through pipes in the vaporizer 600. As this fluid passes around the cooling element 602, the fluid absorbs heat, cooling air in the cooling element 602. After the fluid absorbs the heat, the fluid can pass through a heat exchanger which transfers the heat from the fluid to air blowing through the heat exchanger. By way of further example, the cooling element 602 can comprise a chemical cooling system that utilizes an endothermic reaction. An example of an endothermic reaction is dissolving ammonium nitrate in water. Such endothermic process is used in instant cold packs. These cold packs have a strong outer plastic layer that holds a bag of water and a chemical, or mixture of chemicals, that result in an endothermic reaction when dissolved in water. When the cold pack is squeezed, the inner bag of water breaks and the water mixes with the chemicals. The cold pack starts to cool as soon as the inner bag is broken, and stays cold for over an hour. Many instant cold packs contain ammonium nitrate. When ammonium nitrate is dissolved in water, it splits into positive ammonium ions and negative nitrate ions. In the process of dissolving, the water molecules contribute energy, and as a result, the water cools down. Thus, the vaporizer 600 can comprise a chamber for receiving the cooling element 602 in the form of a "cold pack." The cold pack can be activated prior to insertion into the vaporizer 600 or can be activated after insertion through use of a button/switch and the like to mechanically activate the cold pack inside the vaporizer 400.

In an aspect, the cooling element 602 can be selectively moved within the vaporizer 600 to control the temperature of the air mixing with vapor. For example, the cooling element 602 can be moved closer to the exhaust port 212 or further from the exhaust port 212 to regulate temperature. In another aspect, insulation can be incorporated as needed to maintain the integrity of heating and cooling, as well as absorbing any unwanted condensation due to internal or external conditions, or a combination thereof. The insulation can also be selectively moved within the vaporizer 600 to control the temperature of the air mixing with vapor. For example, the insulation can be moved to cover a portion, none, or all of the cooling element 602 to regulate temperature.

Figure 7:
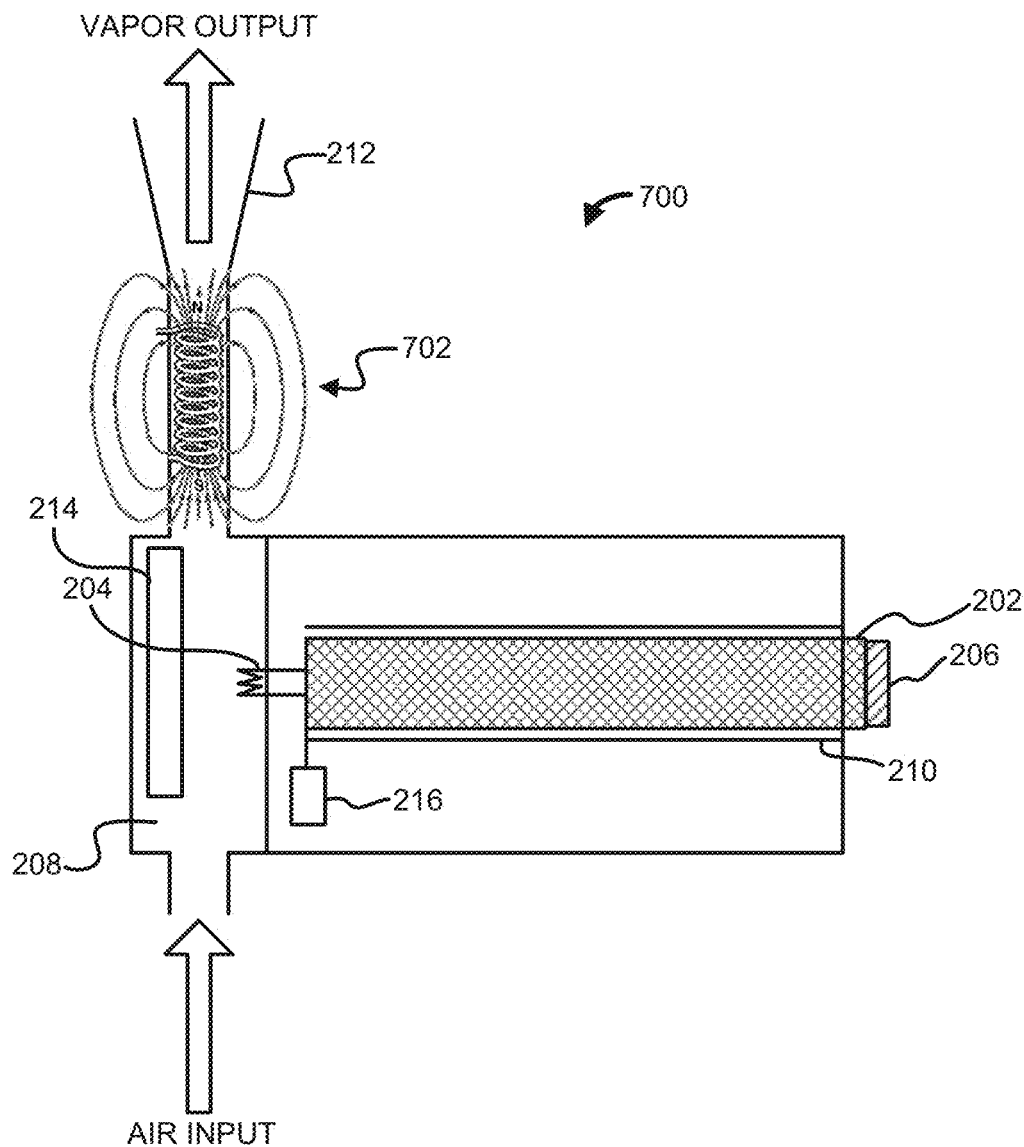
FIG. 7 illustrates another exemplary vaporizer configured for smooth vapor delivery.

FIG. 7 illustrates a vaporizer 700 that comprises elements in common with the vaporizer 200. The vaporizer 700 can optionally comprise the heating casing 402 (not shown) and/or the cooling element 602 (not shown). The vaporizer 700 can comprise a magnetic element 702. The magnetic element 702 can apply a magnetic field to vapor after exiting the mixing chamber 208. The magnetic field can cause positively and negatively charged particles in the vapor to curve in opposite directions, according to the Lorentz force law with two particles of opposite charge. The magnetic field can be created by at least one of an electric current generating a charge or a pre-charged magnetic material deployed within the vapor device 100. In an aspect, the magnetic element 702 can be built into the mixing chamber 208, the cooling element 602, the heating casing 402, or can be a separate magnetic element 702.

Figure 8:
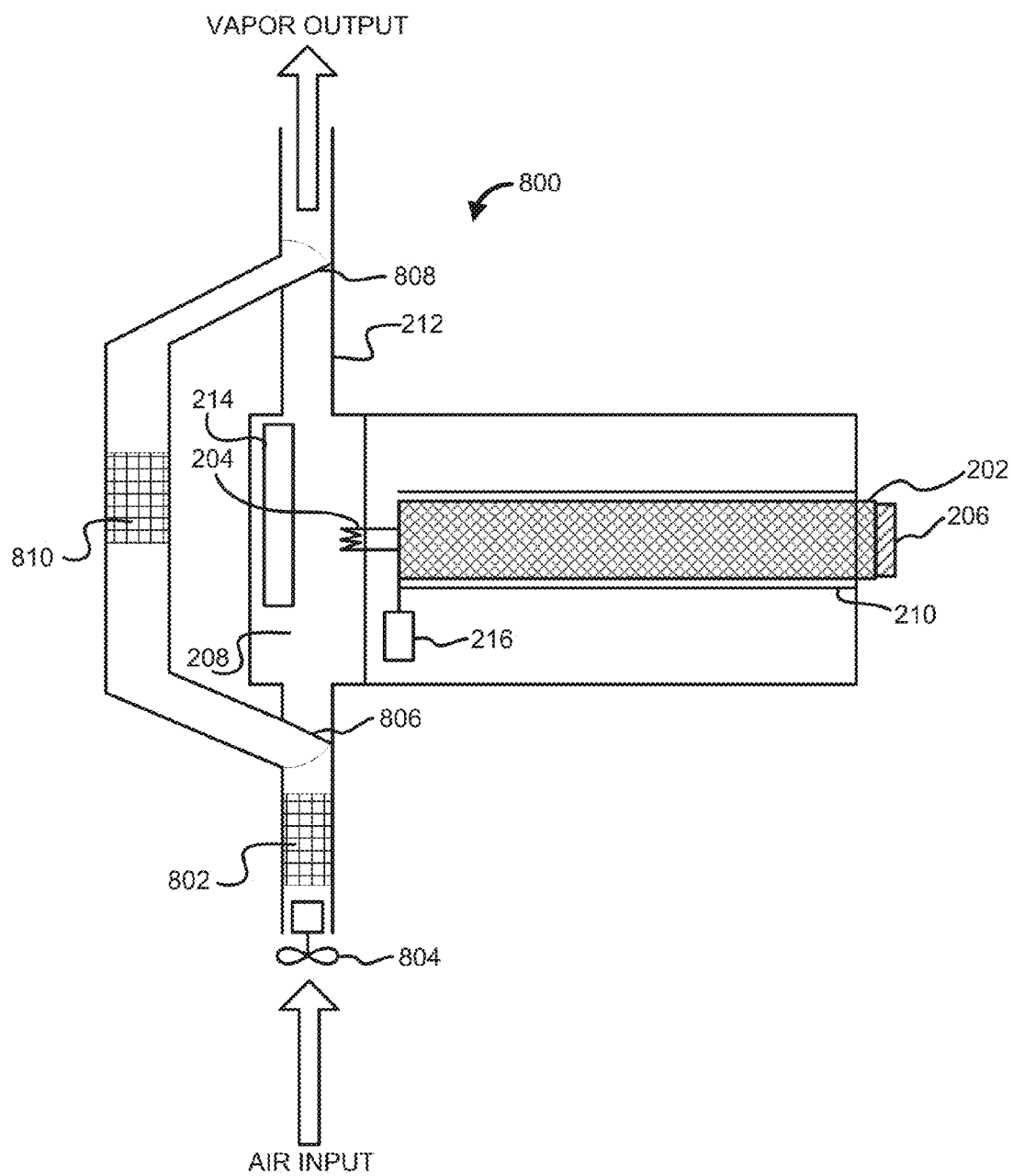
FIG. 8 illustrates an exemplary vaporizer configured for filtering air.

FIG. 8 illustrates a vaporizer 800 that comprises elements in common with the vaporizer 200. In an aspect, the vaporizer 800 can comprise a filtration element 802. The filtration element 802 can be configured to remove (e.g., filter, purify, etc) contaminants from air entering the vaporizer 800. The filtration element 802 can optionally comprise a fan 804 to assist in delivering air to the filtration element 802. The vaporizer 800 can be configured to intake air into the filtration element 802, filter the air, and pass the filtered air to the mixing chamber 208 for use in vaporizing the one or more vaporizable or non-vaporizable materials. In another aspect, the vaporizer 800 can be configured to intake air into the filtration element 802, filter the air, and bypass the mixing chamber 208 by engaging a door 806 and a door 808 to pass the filtered air directly to the exhaust port 212 for inhalation by a user. In an aspect, filtered air that bypasses the mixing chamber 208 by engaging the door 806 and the door 808 can pass through a second filtration element 810 to further remove (e.g., filter, purify, etc) contaminants from air entering the vaporizer 800. In an aspect, the vaporizer 800 can be configured to deploy and/or mix a proper/safe amount of oxygen which can be delivered either via the one or more replaceable cartridges 206 or via air pumped into a mask from external air and filtered through the filtration element 802 and/or the filtration element 810.

In an aspect, the filtration element 802 and/or the filtration element 810 can comprise cotton, polymer, wool, satin, meta materials and the like. The filtration element 802 and/or the filtration element 810 can comprise a filter material that at least one airborne particle and/or undesired gas by a mechanical mechanism, an electrical mechanism, and/or a chemical mechanism. The filter material can comprise one or more pieces of, a filter fabric that can filter out one or more airborne particles and/or gasses. The filter fabric can be a woven and/or non-woven material. The filter fabric can be made from natural fibers (e.g., cotton, wool, etc.) and/or from synthetic fibers (e.g., polyester, nylon, polypropylene, etc.). The thickness of the filter fabric can be varied depending on the desired filter efficiencies and/or the region of the apparel where the filter fabric is to be used. The filter fabric can be designed to filter airborne particles and/or gasses by mechanical mechanisms (e.g., weave density), by electrical mechanisms (e.g., charged fibers, charged metals, etc.), and/or by chemical mechanisms (e.g., absorptive charcoal particles, adsorptive materials, etc.). In as aspect, the filter material can comprise electrically charged fibers such as, but not limited to, FILTRETE by 3M. In another aspect, the filter material can comprise a high density material similar to material used for medical masks which are used by medical personnel in doctors' offices, hospitals, and the like. In an aspect, the filter material can be treated with an anti-bacterial solution and/or otherwise made from anti-bacterial materials. In another aspect, the filtration element 802 and/or the filtration element 810 can comprise electrostatic plates, ultraviolet light, a HEPA filter, combinations thereof, and the like.

Figure 9:
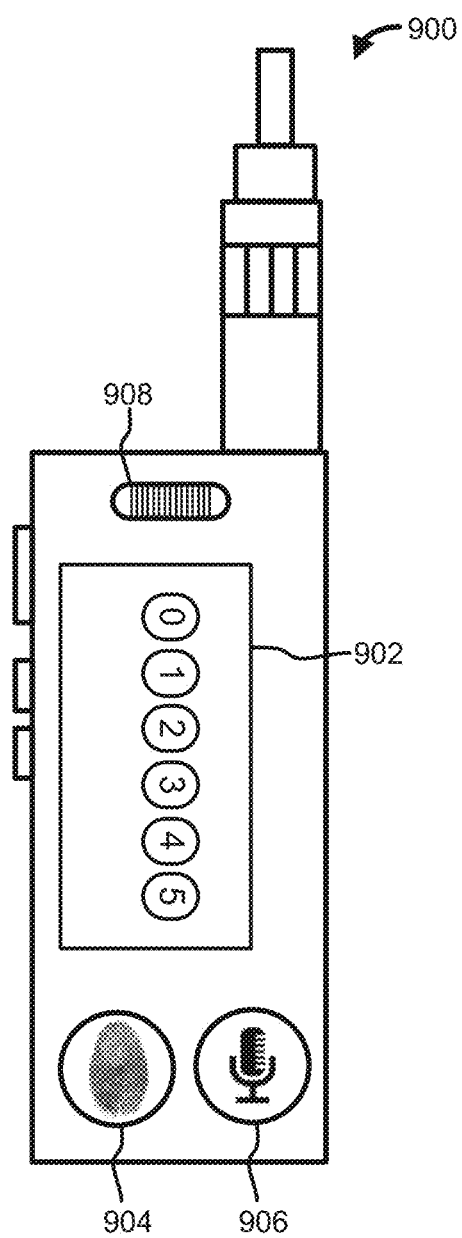
FIG. 9 illustrates an interface of an exemplary electronic vapor device.

FIG. 9 illustrates an exemplary vapor device 900. The exemplary vapor device 900 can comprise the vapor device 100 and/or any of the vaporizers disclosed herein. The exemplary vapor device 900 illustrates a display 902. The display 902 can be a touchscreen. The display 902 can be configured to enable a user to control any and/or all functionality of the exemplary vapor device 900. For example, a user can utilize the display 902 to enter a pass code to lock and/or unlock the exemplary vapor device 900. The exemplary vapor device 900 can comprise a biometric interface 904. For example, the biometric interface 904 can comprise a fingerprint scanner, an eye scanner, a facial scanner, and the like. The biometric interface 904 can be configured to enable a user to control any and/or all functionality of the exemplary vapor device 900. The exemplary vapor device 900 can comprise an audio interface 906. The audio interface 906 can comprise a button that, when engaged, enables a microphone 908. The microphone 908 can receive audio signals and provide the audio signals to a processor for interpretation into one or more commands to control one or more functions of the exemplary vapor device 900.

Figure 10:
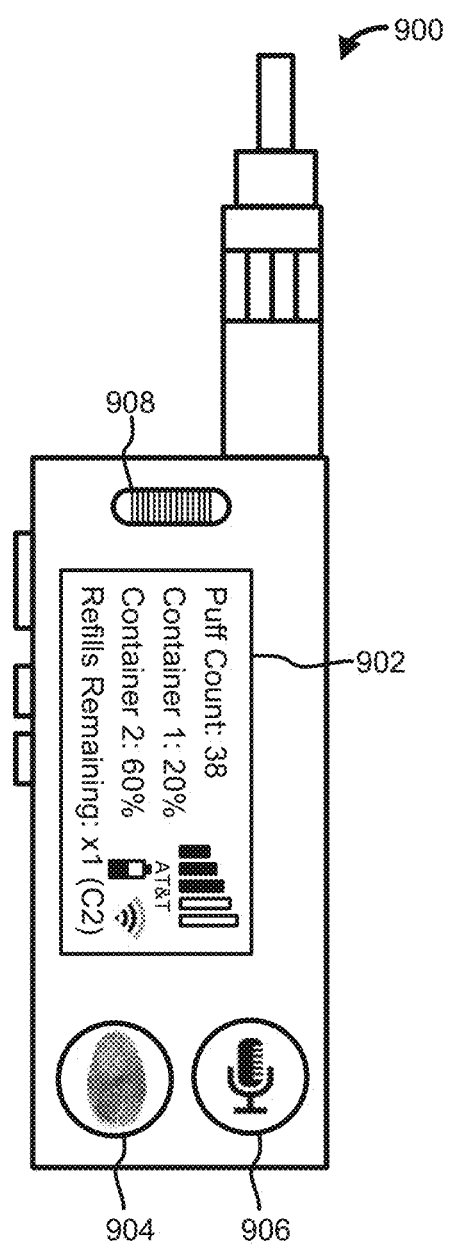
FIG. 10 illustrates another interface of an exemplary electronic vapor device.

FIG. 10 illustrates exemplary information that can be provided to a user via the display 902 of the exemplary vapor device 900. The display 902 can provide information to a user such as a puff count, an amount of vaporizable material remaining in one or more containers, battery remaining, signal strength, combinations thereof, and the like. In an aspect, the information displayed can be related to a disposition signal. For example, the exemplary vapor device 900 can receive a disposition signal authorizing 38 puffs until the user will be required to conduct a financial transaction to receive authorization for more puffs. The display 902 can indicate, for example, that the user has one or more refills remaining. In the example shown in FIG. 10 the user has one refill remaining on container two, after which the user will need to request a disposition signal to refill container two (or container 1) via an internal reservoir.

Figure 11:
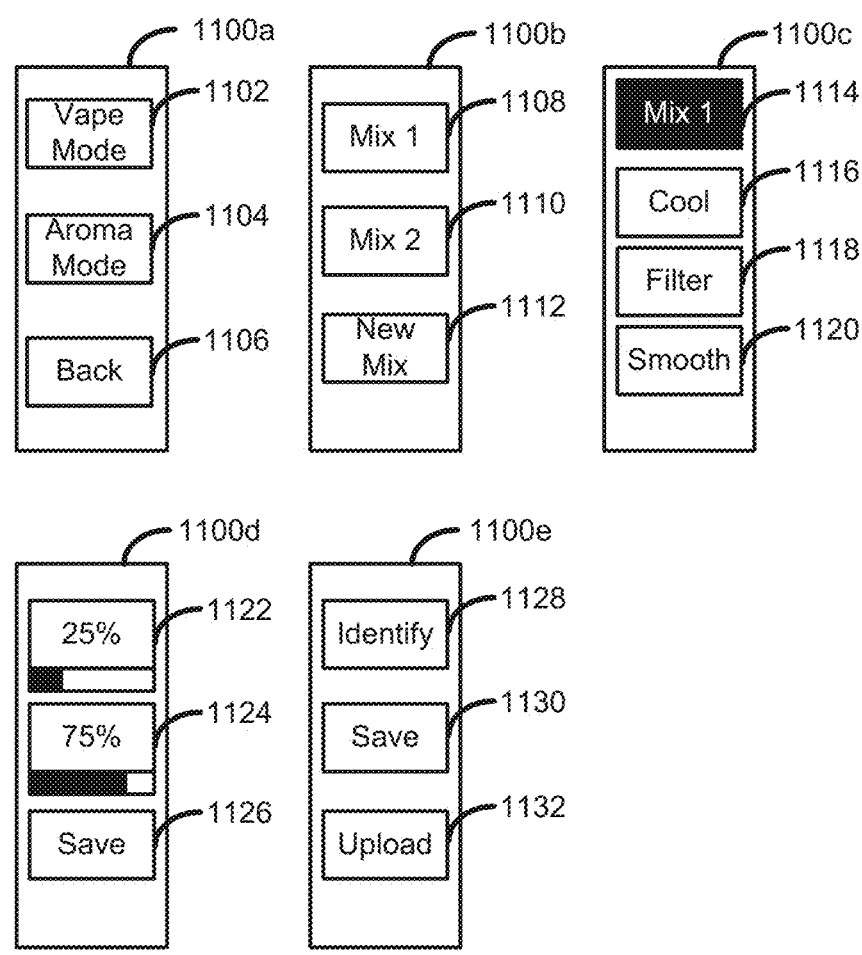
FIG. 11 illustrates several interfaces of an exemplary electronic vapor device.

FIG. 11 illustrates a series of user interfaces that can be provided via the display 902 of the exemplary vapor device 900. In an aspect, the exemplary vapor device 900 can be configured for one or more of multi-mode vapor usage. For example, the exemplary vapor device 900 can be configured to enable a user to inhale vapor (vape mode) or to release vapor into the atmosphere (aroma mode). User interface 1100*a* provides a user with interface elements to select which mode the user wishes to engage, a Vape Mode 1102, an Aroma Mode 1104, or an option to go back 1106 and return to the previous screen. The interface element Vape Mode 1102 enables a user to engage a vaporizer to generate a vapor for inhalation. The interface element Aroma Mode 1104 enables a user to engage the vaporizer to generate a vapor for release into the atmosphere.

In the event a user selects the Vape Mode 1102, the exemplary vapor device 900 will be configured to vaporize material and provide the resulting vapor to the user for inhalation. The user can be presented with user interface 1100*b* which provides the user an option to select interface elements that will determine which vaporizable material to vaporize. For example, an option of Mix 1 1108, Mix 2 1110, or a New Mix 1112. The interface element Mix 1 1108 enables a user to engage one or more containers that contain vaporizable material in a predefined amount and/or ratio. In an aspect, a selection of Mix 1 1108 can result in the exemplary vapor device 900 engaging a single container containing a single type of vaporizable material or engaging a plurality of containers containing a different types of vaporizable material in varying amounts. The interface element Mix 2 1110 enables a user to engage one or more containers that contain vaporizable material in a predefined amount and/or ratio. In an aspect, a selection of Mix 2 1110 can result in the exemplary vapor device 900 engaging a single container containing a single type of vaporizable material or engaging a plurality of containers containing a different types of vaporizable material in varying amounts. In an aspect, a selection of New Mix 1112 can result in the exemplary vapor device 900 receiving a new mixture, formula, recipe, etc. . . . of vaporizable materials and/or engage one or more containers that contain vaporizable material in the new mixture.

Upon selecting, for example, the Mix 1 1108, the user can be presented with user interface 1100*c*. User interface 1100*c* indicates to the user that Mix 1 has been selected via an indicator 1114. The user can be presented with options that control how the user wishes to experience the selected vapor. The user can be presented with interface elements Cool 1116, Filter 1118, and Smooth 1120. The interface element Cool 1116 enables a user to engage one or more cooling elements to reduce the temperature of the vapor. The interface element Filter 1118 enables a user to engage one or more filter elements to filter the air used in the vaporization process. The interface element Smooth 1120 enables a user to engage one or more heating casings, cooling elements, filter elements, and/or magnetic elements to provide the user with a smoother vaping experience.

Upon selecting New Mix 1112, the user can be presented with user interface 1100*d*. User interface 1100*d* provides the user with a container one ratio interface element 1122, a container two ratio interface element 1124, and Save 1126. The container one ratio interface element 1122 and the container two ratio interface element 1124 provide a user the ability to select an amount of each type of vaporizable material contained in container one and/or container two to utilize as a new mix. The container one ratio interface element 1122 and the container two ratio interface element 1124 can provide a user with a slider that adjusts the percentages of each type of vaporizable material based on the user dragging the slider. In an aspect, a mix can comprise 100% on one type of vaporizable material or any percent combination (e.g., 50/50, 75/25, 85/15, 95/5, etc. . . . ). Once the user is satisfied with the new mix, the user can select Save 1126 to save the new mix for later use.

In the event a user selects the Aroma Mode 1104, the exemplary vapor device 900 will be configured to vaporize material and release the resulting vapor into the atmosphere. The user can be presented with user interface 1100*b*, 1100*c*, and/or 1100*d* as described above, but the resulting vapor will be released to the atmosphere.

In an aspect, the user can be presented with user interface 1100*e*. The user interface 1100*e* can provide the user with interface elements Identify 1128, Save 1130, and Upload 1132. The interface element Identify 1128 enables a user to engage one or more sensors in the exemplary vapor device 900 to analyze the surrounding environment. For example, activating the interface element Identify 1128 can engage a sensor to determine the presence of a negative environmental condition such as smoke, a bad smell, chemicals, etc. Activating the interface element Identify 1128 can engage a sensor to determine the presence of a positive environmental condition, for example, an aroma. The interface element Save 1130 enables a user to save data related to the analyzed negative and/or positive environmental condition in memory local to the exemplary vapor device 900. The interface element Upload 1132 enables a user to engage a network access device to transmit data related to the analyzed negative and/or positive environmental condition to a remote server for storage and/or analysis.

Figure 12:
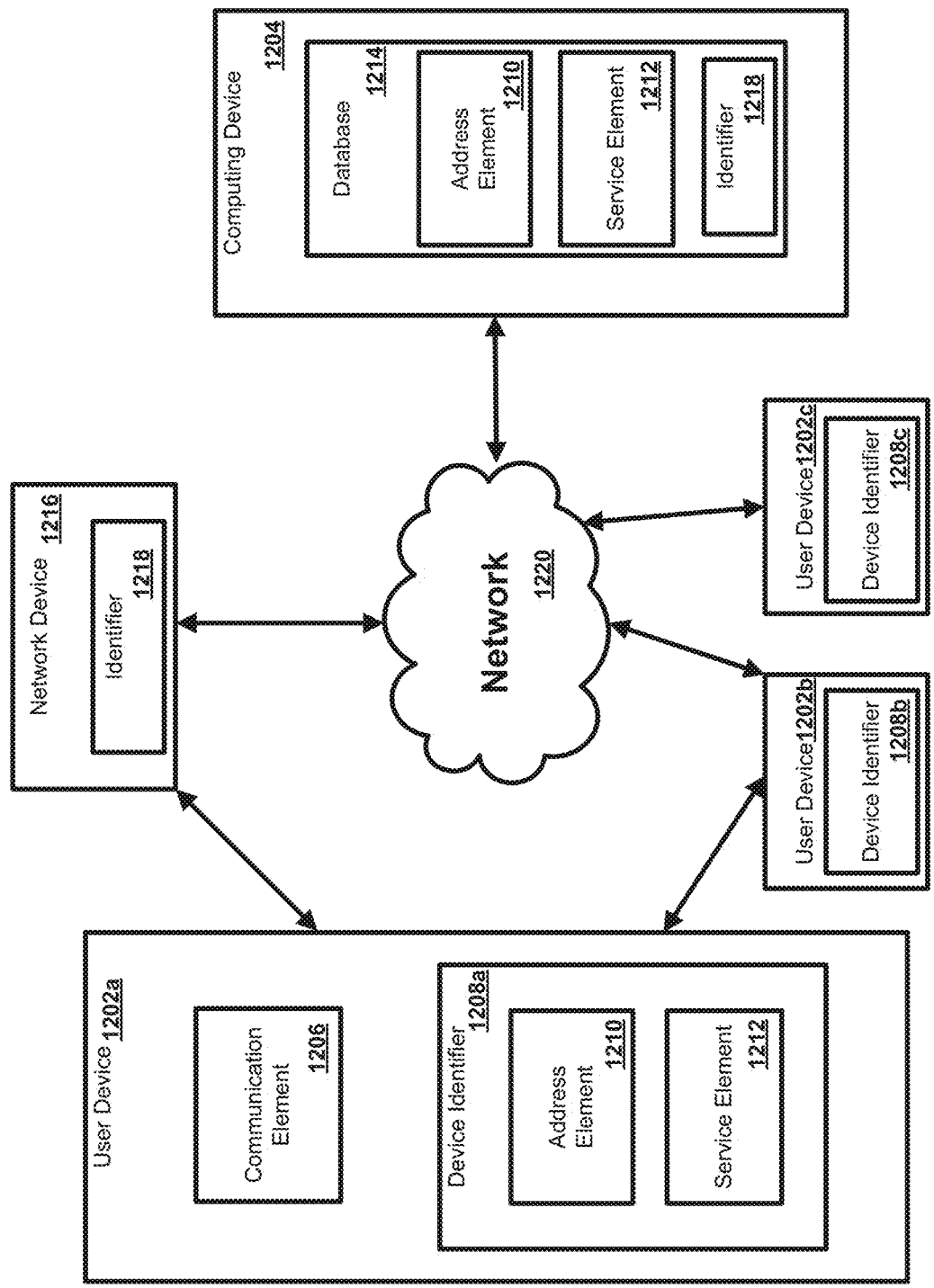
FIG. 12 illustrates an exemplary operating environment.

In one aspect of the disclosure, a system can be configured to provide services such as network-related services to a user device. FIG. 12 illustrates various aspects of an exemplary environment in which the present methods and systems can operate. The present disclosure is relevant to systems and methods for providing services to a user device, for example, electronic vapor devices which can include, but are not limited to, a vape-bot, micro-vapor device, vapor pipe, e-cigarette, hybrid handset and vapor device, and the like. Other user devices that can be used in the systems and methods include, but are not limited to, a smart watch (and any other form of "smart" wearable technology), a smartphone, a tablet, a laptop, a desktop, and the like. In an aspect, one or more network devices can be configured to provide various services to one or more devices, such as devices located at or near a premises. In another aspect, the network devices can be configured to recognize an authoritative device for the premises and/or a particular service or services available at the premises. As an example, an authoritative device can be configured to govern or enable connectivity to a network such as the Internet or other remote resources, provide address and/or configuration services like DHCP, and/or provide naming or service discovery services for a premises, or a combination thereof. Those skilled in the art will appreciate that present methods can be used in various types of networks and systems that employ both digital and analog equipment. One skilled in the art will appreciate that provided herein is a functional description and that the respective functions can be performed by software, hardware, or a combination of software and hardware.

The network and system can comprise a user device 1202a, 1202b, and/or 1202c in communication with a computing device 1204 such as a server, for example. The computing device 1204 can be disposed locally or remotely relative to the user device 1202a, 1202b, and/or 1202c. As an example, the user device 1202a, 1202b, and/or 1202c and the computing device 1204 can be in communication via a private and/or public network 1220 such as the Internet or a local area network. Other forms of communications can be used such as wired and wireless telecommunication channels, for example. In another aspect, the user device 1202a, 1202b, and/or 1202c can communicate directly without the use of the network 1220 (for example, via Bluetooth®, infrared, and the like).

In an aspect, the user device 1202a, 1202b, and/or 1202c can be an electronic device such as an electronic vapor device (e.g., vape-bot, micro-vapor device, vapor pipe, e-cigarette, hybrid handset and vapor device), a smartphone, a smart watch, a computer, a smartphone, a laptop, a tablet, a set top box, a display device, or other device capable of communicating with the computing device 1204. As an example, the user device 1202a, 1202b, and/or 1202c can comprise a communication element 1206 for providing an interface to a user to interact with the user device 1202a, 1202b, and/or 1202c and/or the computing device 1204. The communication element 1206 can be any interface for presenting and/or receiving information to/from the user, such as user feedback. An example interface can be communication interface such as a web browser (e.g., Internet Explorer, Mozilla Firefox, Google Chrome, Safari, or the like). Other software, hardware, and/or interfaces can be used to provide communication between the user and one or more of the user device 1202a, 1202b, and/or 1202c and the computing device 1204. In an aspect, the user device 1202a, 1202b, and/or 1202c can have at least one similar interface quality such as a symbol, a voice activation protocol, a graphical coherence, a startup sequence continuity element of sound, light, vibration or symbol. In an aspect, the interface can comprise at least one of lighted signal lights, gauges, boxes, forms, words, video, audio scrolling, user selection systems, vibrations, check marks, avatars, matrix', visual images, graphic designs, lists, active calibrations or calculations, 2D interactive fractal designs, 3D fractal designs, 2D and/or 3D representations of vapor devices and other interface system functions.

As an example, the communication element 1206 can request or query various files from a local source and/or a remote source. As a further example, the communication element 1206 can transmit data to a local or remote device such as the computing device 1204. In an aspect, data can be shared anonymously with the computing device 1204. The data can be shared over a transient data session with the computing device 1204. The transient data session can comprise a session limit. The session limit can be based on one or more of a number of puffs, a time limit, and a total quantity of vaporizable material. The data can comprise usage data and/or a usage profile. The computing device 1204 can destroy the data once the session limit is reached.

In an aspect, the user device 1202a, 1202b, and/or 1202c can be associated with a user identifier or device identifier 1208a, 1208b, and/or 1208c. As an example, the device identifier 1208a, 1208b, and/or 1208c can be any identifier, token, character, string, or the like, for differentiating one user or user device (e.g., user device 1202a, 1202b, and/or 1202c) from another user or user device. In a further aspect, the device identifier 1208a, 1208b, and/or 1208c can identify a user or user device as belonging to a particular class of users or user devices. As a further example, the device identifier 1208a, 1208b, and/or 1208c can comprise information relating to the user device such as a manufacturer, a model or type of device, a service provider associated with the user device 1202a, 1202b, and/or 1202c, a state of the user device 1202a, 1202b, and/or 1202c, a locator, and/or a label or classifier. Other information can be represented by the device identifier 1208a, 1208b, and/or 1208c.

In an aspect, the device identifier 1208a, 1208b, and/or 1208c can comprise an address element 1210 and a service element 1212. In an aspect, the address element 1210 can comprise or provide an internet protocol address, a network address, a media access control (MAC) address, an Internet address, or the like. As an example, the address element 1210 can be relied upon to establish a communication session between the user device 1202a, 1202b, and/or 1202c and the computing device 1204 or other devices and/or networks. As a further example, the address element 1210 can be used as an identifier or locator of the user device 1202a, 1202b, and/or 1202c. In an aspect, the address element 1210 can be persistent for a particular network.

In an aspect, the service element 1212 can comprise an identification of a service provider associated with the user device 1202a, 1202b, and/or 1202c and/or with the class of user device 1202a, 1202b, and/or 1202c. The class of the user device 1202a, 1202b, and/or 1202c can be related to a type of device, capability of device, type of service being provided, and/or a level of service. As an example, the service element 1212 can comprise information relating to or provided by a communication service provider (e.g., Internet service provider) that is providing or enabling data flow such as communication services to and/or between the user device 1202a, 1202b, and/or 1202c. As a further example, the service element 1212 can comprise information relating to a preferred service provider for one or more particular services relating to the user device 1202a, 1202b, and/or 1202c. In an aspect, the address element 1210 can be used to identify or retrieve data from the service element 1212, or vice versa. As a further example, one or more of the address element 1210 and the service element 1212 can be stored remotely from the user device 1202a, 1202b, and/or 1202c and retrieved by one or more devices such as the user device 1202*a*, 1202*b*, and/or 1202*c* and the computing device 1204. Other information can be represented by the service element 1212.

In an aspect, the computing device 1204 can be a server for communicating with the user device 1202*a*, 1202*b*, and/or 1202*c*. As an example, the computing device 1204 can communicate with the user device 1202*a*, 1202*b*, and/or 1202*c* for providing data and/or services. As an example, the computing device 1204 can provide services such as data sharing, data syncing, network (e.g., Internet) connectivity, network printing, media management (e.g., media server), content services, streaming services, broadband services, or other network-related services. In an aspect, the computing device 1204 can allow the user device 1202*a*, 1202*b*, and/or 1202*c* to interact with remote resources such as data, devices, and files. As an example, the computing device can be configured as (or disposed at) a central location, which can receive content (e.g., data) from multiple sources, for example, user devices 1202*a*, 1202*b*, and/or 1202*c*. The computing device 1204 can combine the content from the multiple sources and can distribute the content to user (e.g., subscriber) locations via a distribution system.

In an aspect, one or more network devices 1216 can be in communication with a network such as network 1220. As an example, one or more of the network devices 1216 can facilitate the connection of a device, such as user device 1202*a*, 1202*b*, and/or 1202*c*, to the network 1220. As a further example, one or more of the network devices 1216 can be configured as a wireless access point (WAP). In an aspect, one or more network devices 1216 can be configured to allow one or more wireless devices to connect to a wired and/or wireless network using Wi-Fi, Bluetooth or any desired method or standard.

In an aspect, the network devices 1216 can be configured as a local area network (LAN). As an example, one or more network devices 1216 can comprise a dual band wireless access point. As an example, the network devices 1216 can be configured with a first service set identifier (SSID) (e.g., associated with a user network or private network) to function as a local network for a particular user or users. As a further example, the network devices 1216 can be configured with a second service set identifier (SSID) (e.g., associated with a public/community network or a hidden network) to function as a secondary network or redundant network for connected communication devices.

In an aspect, one or more network devices 1216 can comprise an identifier 1218. As an example, one or more identifiers can be or relate to an Internet Protocol (IP) Address IPV4/IPV6 or a media access control address (MAC address) or the like. As a further example, one or more identifiers 1218 can be a unique identifier for facilitating communications on the physical network segment. In an aspect, each of the network devices 1216 can comprise a distinct identifier 1218. As an example, the identifiers 1218 can be associated with a physical location of the network devices 1216.

In an aspect, the computing device 1204 can manage the communication between the user device 1202*a*, 1202*b*, and/or 1202*c* and a database 1214 for sending and receiving data therebetween. As an example, the database 1214 can store a plurality of files (e.g., web pages), user identifiers or records, or other information. In one aspect, the database 1214 can store user device 1202*a*, 1202*b*, and/or 1202*c* usage information (including chronological usage), type of vaporizable and/or non-vaporizable material used, frequency of usage, location of usage, recommendations, communications (e.g., text messages, advertisements, photo messages), simultaneous use of multiple devices, and the like). The database 1214 can collect and store data to support cohesive use, wherein cohesive use is indicative of the use of a first electronic vapor devices and then a second electronic vapor device is synced chronologically and logically to provide the proper specific properties and amount of vapor based upon a designed usage cycle. As a further example, the user device 1202*a*, 1202*b*, and/or 1202*c* can request and/or retrieve a file from the database 1214. The user device 1202*a*, 1202*b*, and/or 1202*c* can thus sync locally stored data with more current data available from the database 1214. Such syncing can be set to occur automatically on a set time schedule, on demand, and/or in real-time. The computing device 1204 can be configured to control syncing functionality. For example, a user can select one or more of the user device 1202*a*, 1202*b*, and/or 1202*c* to never by synced, to be the master data source for syncing, and the like. Such functionality can be configured to be controlled by a master user and any other user authorized by the master user or agreement.

In an aspect, data can be derived by system and/or device analysis. Such analysis can comprise at least by one of instant analysis performed by the user device 1202*a*, 1202*b*, and/or 1202*c* or archival data transmitted to a third party for analysis and returned to the user device 1202*a*, 1202*b*, and/or 1202*c* and/or computing device 1204. The result of either data analysis can be communicated to a user of the user device 1202*a*, 1202*b*, and/or 1202*c* to, for example, inform the user of their eVapor use and/or lifestyle options. In an aspect, a result can be transmitted back to at least one authorized user interface.

In an aspect, the database 1214 can store information relating to the user device 1202*a*, 1202*b*, and/or 1202*c* such as the address element 1210 and/or the service element 1212. As an example, the computing device 1204 can obtain the device identifier 1208*a*, 1208*b*, and/or 1208*c* from the user device 1202*a*, 1202*b*, and/or 1202*c* and retrieve information from the database 1214 such as the address element 1210 and/or the service elements 1212. As a further example, the computing device 1204 can obtain the address element 1210 from the user device 1202*a*, 1202*b*, and/or 1202*c* and can retrieve the service element 1212 from the database 1214, or vice versa. Any information can be stored in and retrieved from the database 1214. The database 1214 can be disposed remotely from the computing device 1204 and accessed via direct or indirect connection. The database 1214 can be integrated with the computing device 1204 or some other device or system. Data stored in the database 1214 can be stored anonymously and can be destroyed based on a transient data session reaching a session limit.

Figure 13:
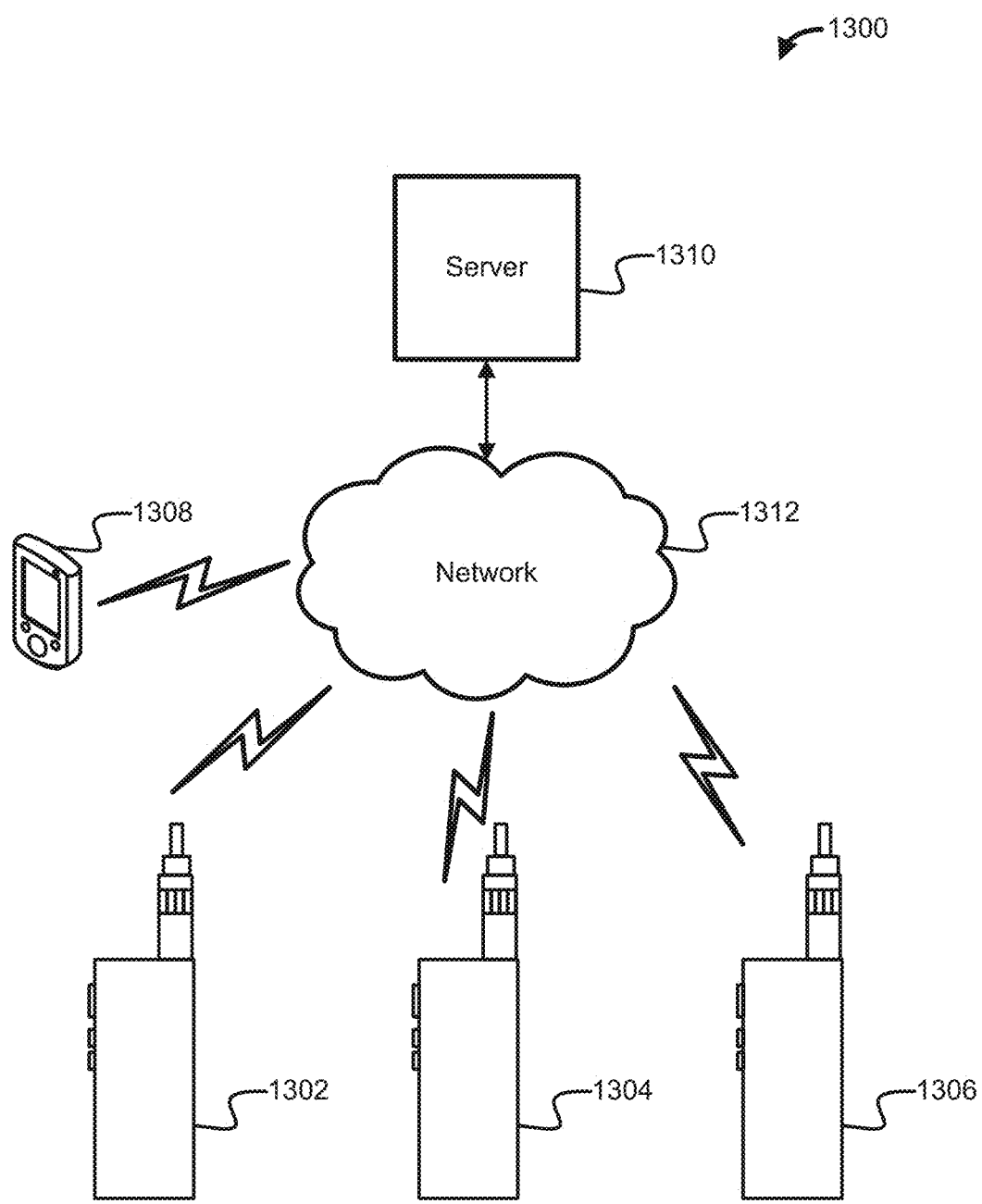
FIG. 13 illustrates another exemplary operating environment.

FIG. 13 illustrates an ecosystem 1300 configured for sharing and/or syncing data such as usage information (including chronological usage), type of vaporizable and/or non-vaporizable material used, frequency of usage, location of usage, recommendations, communications (e.g., text messages, advertisements, photo messages), simultaneous use of multiple devices, and the like) between one or more devices such as a vapor device 1302, a vapor device 1304, a vapor device 1306, and an electronic communication device 1308. In an aspect, the vapor device 1302, the vapor device 1304, the vapor device 1306 can be one or more of an e-cigarette, an e-cigar, an electronic vapor modified device, a hybrid electronic communication handset coupled/integrated vapor device, a micro-sized electronic vapor device, or a robotic vapor device. In an aspect, the electronic communication device 1308 can comprise one or more of a smartphone, a smart watch, a tablet, a laptop, and the like.

In an aspect data generated, gathered, created, etc., by one or more of the vapor device 1302, the vapor device 1304, the vapor device 1306, and/or the electronic communication device 1308 can be uploaded to and/or downloaded from a central server 1310 via a network 1312, such as the Internet. Such uploading and/or downloading can be performed via any form of communication including wired and/or wireless. In an aspect, the vapor device 1302, the vapor device 1304, the vapor device 1306, and/or the electronic communication device 1308 can be configured to communicate via cellular communication, WiFi communication, Bluetooth® communication, satellite communication, and the like. The central server 1310 can store uploaded data and associate the uploaded data with a user and/or device that uploaded the data. The central server 1310 can access unified account and tracking information to determine devices that are associated with each other, for example devices that are owned/used by the same user. The central server 1310 can utilize the unified account and tracking information to determine which of the vapor device 1302, the vapor device 1304, the vapor device 1306, and/or the electronic communication device 1308, if any, should receive data uploaded to the central server 1310.

In an aspect the central server 1310 can manage one or more user accounts and user authorizations to access one or more functions of the vapor device 1302, the vapor device 1304, and the vapor device 1306. The central server 1310 can transmit one or more disposition signals to the vapor device 1302, the vapor device 1304, and the vapor device 1306 to enable or disable one or more components and/or functions of the vapor device 1302, the vapor device 1304, and the vapor device 1306. The disposition signal can comprise one or more of, a command to vaporize the vaporizable material, a command to disable the vaporizer component, a command to enable the vaporizer component, a command to place the vaporizer component in an on-demand state, a command to mix the vaporizable material with another vaporizable material, a command to mix the vaporizable material with a non-vaporizable material, a command to replenish the vaporizable material, a command to deplete the vaporizable material without vaporizing the vaporizable material. The disposition signal can comprise one or more of, a command to dispense the non-vaporizable material, a command to disable the dispenser, a command to enable the dispenser, a command to place the dispenser in an on-demand state, a command to mix the non-vaporizable material with another non-vaporizable material, a command to mix the vaporizable material with the non-vaporizable material, a command to replenish the non-vaporizable material, a command to deplete the non-vaporizable material without dispensing the non-vaporizable material. The central server 1310 can conduct one or more financial transactions in exchange for providing a requested disposition signal to the vapor device 1302, the vapor device 1304, and the vapor device 1306

In an aspect, the uploading and downloading can be performed anonymously. The data can be shared over a transient data session with the central server 1310. The transient data session can comprise a session limit. The session limit can be based on one or more of a number of puffs, a time limit, and a total quantity of vaporizable material. The data can comprise usage data and/or a usage profile. The central server 1310 can destroy the data once the session limit is reached. While the transient data session is active, the central server 1310 can provide a usage profile to one of the vapor device 1302, the vapor device 1304, the vapor device 1306 to control the functionality for the duration of the transient data session.

For example, the vapor device 1302 can be configured to upload usage information related to vaporizable material consumed and the electronic communication device 1308 can be configured to upload location information related to location of the vapor device 1302. The central server 1310 can receive both the usage information and the location information, access the unified account and tracking information to determine that both the vapor device 1302 and the electronic communication device 1308 are associated with the same user. The central server 1310 can thus correlate the user's location along with the type, amount, and/or timing of usage of the vaporizable material. The central server 1310 can further determine which of the other devices are permitted to receive such information and transmit the information based on the determined permissions. In an aspect, the central server 1310 can transmit the correlated information to the electronic communication device 1308 which can then subsequently use the correlated information to recommend a specific type of vaporizable material to the user when the user is located in the same geographic position indicated by the location information.

In another aspect, the central server 1310 can provide one or more social networking services for users of the vapor device 1302, the vapor device 1304, the vapor device 1306, and/or the electronic communication device 1308. Such social networking services include, but are not limited to, messaging (e.g., text, image, and/or video), mixture sharing, product recommendations, location sharing, product ordering, and the like.

Figure 14:
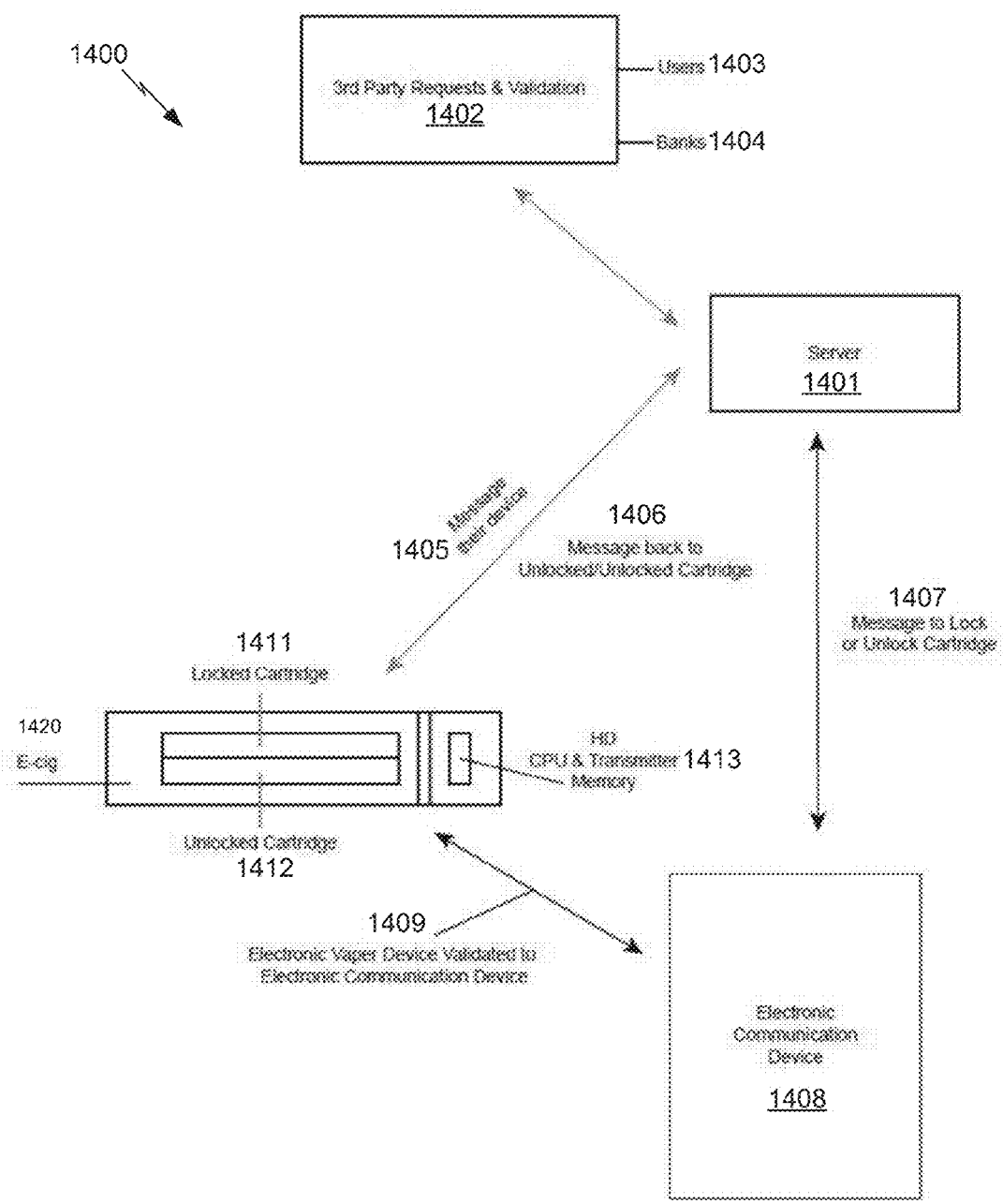
FIG. 14 illustrates an example vaporizer system.

Referring to FIG. 14, remote and contiguous control of access to vapor from a personal vaporizer 1420 (e.g., an e-cigarette) and proscribed usage of differing vapor fluid or other material elements within a personal vaporizer, for example an electronic cigarette (e-cigarette) or the like may be provided by a system 1400. The personal vaporizer 1420 may include an electrical circuit 1413 controlling a vaporizing component of the personal vaporizer according to data received from an external source, e.g., a central server 1401. The electrical circuit 1413 may include, for example, a processor with input/output ports, a transceiver, a memory, and a power source. The electrical circuit 1413 may be coupled to vaporizable material in the device 1420, for example to material in a cartridge 1411, 1412 that may be operatively coupled to the circuit 1413. The cartridge 1411 (or the other cartridge 1412) may, in response to the circuit 1413, place itself in a locked state for a period of time, thereby disabling access to the vaporizable material inside. Likewise, the cartridge 1412 (or the other cartridge 1411) may, in response to the circuit 1413, place itself in an unlocked state for a period of time, thereby disabling access to the vaporizable material inside. Disposition of the vaporizable material in the vaporizer 1420 vaporizes a particular material may thus be controlled based on input from the user, a caregiver, a recommendation system, a social network or other third party, via processor control of a disposition control element (e.g., the cartridges 1411, 1412).

Locking or unlocking of a cartridge may be accomplished through a disposition control mechanism, for example a valve, coupled to an outlet of the cartridge. Activating or deactivating the mechanism, for example by opening a valve or gate, may unlock access to material inside the cartridge. Activating or deactivating the mechanism, for example by closing a valve or gate, may unlock access to material inside the cartridge. Whether the mechanism is activated or deactivated to achieve the desired result may depend on whether the mechanism is a "normally closed" type or a "normally open" type. To open a mechanism of a normally closed type, power may be supplied to an actuator coupled to the mechanism. When the power is cut off, the mechanism will close or otherwise cease to deliver material for vaporizing. To close a mechanism of normally open type, power may be supplied to an actuator coupled to the mechanism. When the power is cut off, the mechanism will open or otherwise deliver material for vaporizing.

The circuit may control dispensing of different vaporizable materials from the cartridges 1411, 1412. For example, as dispensing of a first substance is reduced or increased, one or more replacement substances may be released under control of the vaporizer's electrical circuit 1413 at a correspondingly increased or decreased amount to compensate for the decrease in the first substance. Liquid ports may be used to admit different mixtures of multiple liquids to the vaporizing component, under control of the electrical circuit 1413, or by mechanical means controlled by manual input. Use of a particular vaporizing fluid may be locked or unlocked by one or more switches of the circuit 1413, which may be configured as software, hardware, firmware, or some combination of the foregoing.

The central server 1401 may be used to hold a user ID and protocols or plans for dispensing various vaporizable materials in connection with the user or a particular vaporizer 1420. For example, the server 1401 may correlate a user ID to the user's prescribed or desired conditions for utilizing the personal vaporizer 1420. Control data 1405 may be provided to the personal vaporizer via a receiver in the personal vaporizer or in an auxiliary device such as a docking station or package (not shown). An electrical circuit 1413 of the personal vaporizer 1420 receives the data 1405 and may dispense or mix one or more available fluids in corresponding chambers of the personal vaporizer 1420 to exact specifications as determined by the control data 1405. The control circuit may transmit a message 1406, for example a request to unlock a particular vaporizable material or an e-commerce transaction associated with such request, to the server 1401.

By tracking use of the personal vaporizer 1420 in association with a user identifier at a remote server 1401, a control scheme can be continued uninterrupted when a user switches from one personal vaporizer to a next. For example, an associated electronic communication device 1408 (e.g., a smartphone, tablet device, or docking station) may validate a particular vaporizer 1420 using a handshaking protocol 1409. The communication device 1408 may receive a control message from the server 1401, for example a communication instructing the communication device 1408 to relay a "lock" or "unlock" command to the vaporizer device 1420, relating to any one or both of the cartridges 1411, 1412. Once the device 1420 is validated, the communication device may, for example, provide the lock or unlock commands to the device 1420 and receive a confirmation that the commands are executed.

The communication device 1408 may perform other functions, for example, it may detect that use of one vapor device was stopped before a particular control scheme was fulfilled. Accordingly, when the user begins using a new personal vaporizer, settings for the new vaporizer once initiated will pick up where the old device left off. Likewise, if the user goes back to using the original vaporizer, then the resumed operation of the reused vaporizer will be automatically adjusted to compensate for the user's intervening usage of a different vaporizer. Thus, a dosing or use schedule may be maintained in a seamless way across any number of transitions between different personal vaporizers. This may be particularly useful for implementing controlled use of disposable e-cigarettes or the like, or other applications involving use of different vaporizers by the same user. A biometric component (not shown) may utilize biometric data collected via the vaporizer 1420 or ancillary device to track use by an identified user across multiple vaporizer devices.

Each personal vaporizer 1420 may collect usage data during use and transmits the data to a designated network address, for example an address for a data management server 1401. For example, the vaporizer may monitor levels of vaporizing fluids remaining in its internal reservoirs, using one or more sensors, and provide monitoring data to a data server via a wired or wireless port to a communication network. Usage data can be made available to the user, caregivers, loved ones and others in the users designated social network, by distribution from the data server, for example, to a third party node 1402. In this way a user or group of users 1403 can also be connected through their smart devices or via rudimentary interfaces on the vapor device to communicate with each other and offer friendship, love, humor, support, and other social benefits. A third party node 1402 may also connect the user with e-commerce sires, for example banks 1404, enabling commercial transactions for replenishing vaporizing fluid levels in the device 1420.

A control scheme based on monitoring data may trigger a communication to the user via the personal vaporizer 1420 or other user interface. Such communication may include inquiring whether a user is interested in replenishing one or more vaporizable materials, once a supply or prescribed amount of material has been consumed. A communication session directed at resupplying material or reauthorizing a prescribed use of material may include a remote transaction option enabling the user to complete a commercial or other transaction with third part node 1402 enabling supply of and/or vaporization of additional material, and/or to further use of the personal vaporizer itself. This may include, for example, providing information via the vaporizer or other user interface to a nearby kiosk or the like to enable resupply of additional vaporizable material to the personal vaporizer.

In an aspect, a user may be enabled to make a payment by electronic communication via the e-cigarette device 1420 or cooperating wireless device so that a resupply transaction at a specified supply kiosk or apparatus can be prepaid, in cooperation with a remote payment component. For example, a transaction server 1401 may provide a proof-of-payment certificate received from the third party node 1402 to the personal vaporizer via an electronic communication, which may be stored in a memory component of the vaporizer. The personal vaporizer may then provide the payment certificate to enable dispensing of the desired substance at the point of supply. Refilling of vaporizable fluids may occur via a refill port (not shown) included on or in the personal vaporizer 1420.

Various electronic personal vaporizing devices are known in the art, and are frequently being improved on. For example, details of a recent "Vapor Delivery Device" are disclosed by the inventor hereof in U.S. Patent Publication No. 2015/0047661, incorporated herein by reference. While the referenced publication provides a pertinent example of a personal vaporizer, it should be appreciated that various different designs for personal vaporizing devices are known in the art and may be adapted for use with the technology disclosed herein by one of ordinary skill. In addition, similar portable and personal devices for nebulizing liquids to create a mist for inhalation should be considered as generally encompassed within the meaning of "personal vaporizer" as used herein.

Figure 15:
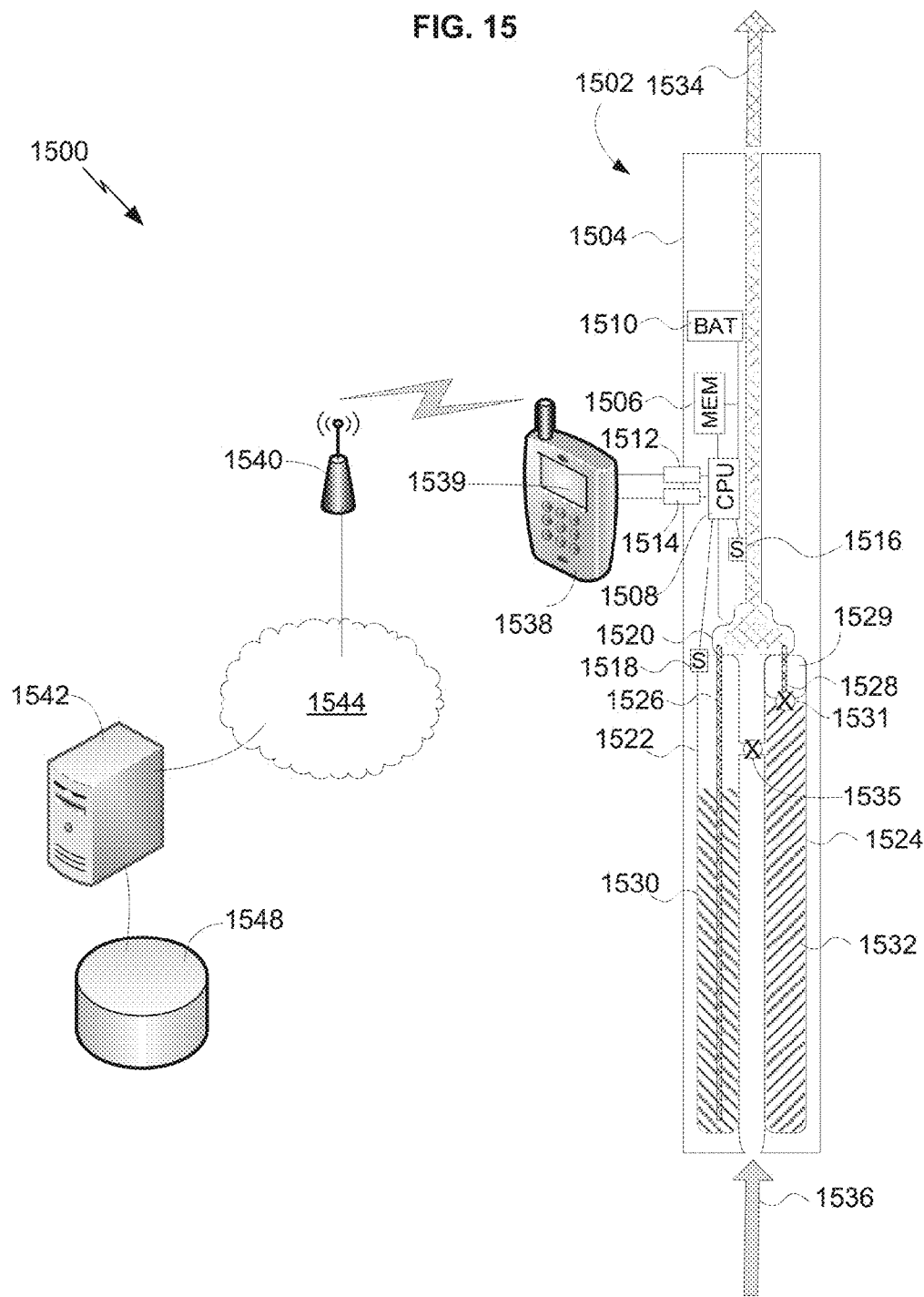
FIG. 15 illustrates an example vaporizer system.

Referring to FIG. 15, alternative aspects of a system 1500 for handling or disposing of a vaporizable material in an electronic vaporizer are illustrated. The system 1500 may include an assembly 1502 for vaporizing a vaporizing fluid at a controlled rate, and for combining vaporization of two or more different fluids in a controlled manner. The apparatus 1502 may include at least one vaporizable material 1530 coupled to an electrical circuit (1508, 1506, 1510) configured for controlling disposition of the vaporizable material. For example, the assembly 1502 may include at least one container 1522 holding the vaporizable material 1530, sometimes referred to herein as a "first" container 1522 and "first" vaporizable material. The processor 1508 may be coupled to the electrical circuit, configured to control at least an aspect of the disposition.

In an aspect, the vaporizable material may be a fluid, such as a compressed gas, compressed liquid (e.g., a liquefied gas), or uncompressed liquid. Various suitable fluids are known in the art, for example, solutions of nicotine in glycerin, with or without flavor-enhancing agents, are known. In the alternative, or in addition, the first vaporizable material may be, or may include, a solid material. For embodiments using uncompressed liquids, the container 1522 may include a wick 1526 that carries the liquid to the vaporizing component 1520. Although the wick 1526 is shown only in the center of the container 1522 for illustrative clarity, it should be appreciated that the wick may substantially fill the container 1522. The container 1522 may be made of any suitable structural material, for example, an organic polymer, metal, ceramic, composite or glass material. Structural plastics may be preferred for disposable embodiments.

The apparatus 1502 may include one or more additional or "second" containers 1524 (one of potentially many shown), each configured similarly with a wick if suitable for the particular second vaporizable material 1532 being contained. In the illustrated example, a wick 1528 leading to the vaporizing component 1520 is positioned only in a dispensing chamber 1529 that is coupled to the container 1524 and the second material 1532 via a disposition control mechanism 1531, for example a valve. The flow control or other disposition control mechanism 1531 may be controlled by the processor 1508 and other circuit elements of the apparatus 1502. Thus, the disposition control mechanism 1531 may be operatively interposed between the electrical circuit and the vaporizable material 1532, configured to actuate the disposition of the material. The disposition control mechanism 1531 may be, or may include, any one or more of a valve, a membrane, a foil barrier, a stationary wick, a movable wick, a bubble jet, a piezoelectric pump, a microfluidic pump, a mechanical pump, or a heater. A pump is represented diagrammatically in FIG. 15. The processor 1508 and/or other circuit element may cause the disposition control mechanism 1531 to be activated, dispensing a controlled amount of the material 1532 into the dispensing chamber 1528, where it can be absorbed by the wick 1528 and delivered to the vaporizing component 1520.

In an alternative, or in addition, the second container 1524 may be coupled to the first container 1522 via a coupling under the control of another disposition control mechanism 1535. The disposition control mechanism 1535 may likewise be, or may include, any one or more of a valve, a membrane, a foil barrier, a stationary wick, a movable wick, a bubble jet, a piezoelectric pump, a microfluidic pump, or a mechanical pump. The processor 1508 and/or other circuit element may cause the disposition control mechanism 1535 to be activated, dispensing a controlled amount of the material 1532 into the first container 1522, where it can be absorbed by the wick 1526 and delivered to the vaporizing component 1520. In this way, a supply of the material in the first container 1522 may be replenished in a controlled way.

Activation of vaporization may be controlled by application of suction at the inhalation port at exit arrow 1534. A drop in pressure at the vaporizing component 1520 may be electronically or mechanically sensed by the electrical circuit and/or processor 1508, causing vaporization of a mix of fluid components determined by the electrical circuit. The suction may activate power to the vaporizing component 1520, with the mix of vaporizable materials 1530, 1532 controlled by the electrical circuit. To the end user, the device 1502 provides the satisfaction of vapor production in response to suction applied, while the composition of the vapor is controlled, and may vary with time. Thus, for example, the user may continue to use the vaporizers for as long as desired or until exhausting power or fluid reserves (whichever comes first), without exceeding a desired dose of nicotine or other physiologically active substance being administered by vaporization via the device 1502.

In an aspect, the electrical circuit including the processor 1508 may be configured for controlling disposition of the vaporizable material prior to vaporization thereof. This aspect has been illustrated by the examples described above. In an alternative aspect, the electrical circuit including the processor 1508 may be configured for controlling disposition of the vaporizable material after vaporization thereof. For example, a vaporizable or non-vaporizable material may be introduced into an output stream downstream of the vaporizer 1520. In an aspect, the electronic vaporizer comprises a dispenser coupled to the electric circuit for dispensing the at least one of a vaporizable material or a non-vaporizable material in at least one of an inhalable form or an ingestible form. The dispenser may combine a combination of elements, for example a vaporizer 1520 and outlet or inhalation port for a vaporizable material, or a pump and discharge port (not shown) for a non-vaporizable material.

A vaporizer 1520 may be coupled to the first container 1522 and to any additional containers, e.g., second container 1524. For example, coupling may be via wicks 1526, 1524, via a valve, or by some other structure. The coupling mechanism may operate independently of gravity, such as by capillary action or pressure drop through a valve. The vaporizer 1520 is configured to vaporize the vaporizable material from the first container 1522 and any additional containers 1524 at controlled rates; in operation, the vaporizer vaporizes or nebulizes the material, producing an inhalable mist. In embodiments, the vaporizer may include a heater coupled to a wick, or a heated wick. A heating circuit may include a nickel-chromium wire or the like, with a temperature sensor (not shown) such as a thermistor or thermocouple. Within definable limits, by controlling suction-activated power to the heating element, a rate of vaporization may be controlled. At minimum, control may be provided between no power (off state) and one or more powered states. Other control mechanisms may also be suitable.

A processor 1508 is coupled to the vaporizer via an electrical circuit, configured to control a rate at which the vaporizer 1520 vaporizes the vaporizable material and disposition of at least one of the materials 1530, 1532 via one or more disposition control mechanisms 1531, 1535. In operation, the processor supplies a control signal to the vaporizer 1520 that controls the rate of vaporization and/or a different control signal that controls operation of the disposition control mechanisms 1531, 1535. A receiver port 1512 is coupled to the processor, and the processor may receives data determining the rate and/or disposition of material from the receiver port. Thus, the vaporization rate and disposition of one or more materials is remotely controllable, by providing the data. The processor 1508 may be, or may include, any suitable microprocessor or microcontroller, for example, a low-power application-specific controller (ASIC) designed for the task of controlling a vaporizer as described herein, or (less preferably) a general-purpose central processing unit, for example, one based on 80×86 architecture as designed by Intel™ or AMD™, or a system-on-a-chip as designed by ARM™ or other chip designers. The processor 1508 may be communicatively coupled to auxiliary devices or modules of the vaporizing apparatus 1502, using a bus or other coupling. Optionally, the processor 1508 and some or all of its coupled auxiliary devices or modules may be housed within or coupled to a housing 1504, substantially enclosing the containers 1524, 1524, the vaporizer 1520, the processor 1508, the receiver port 1512, and other illustrated components. The assembly 1502 and housing 1504 may be configured together in a form factor of an electronic cigarette, an electronic cigar, an electronic hookah, a hand-held personal vaporizer, or other desired form.

In related aspects, the assembly 1502 includes a memory device 1506 coupled to the processor 1508, and other elements making up an electric control circuit. The memory device 1506 may include a random access memory (RAM) holding program instructions and data for rapid execution or processing by the processor during control of the vaporizer 1502. When the vaporizer 1502 is powered off or in an inactive state, program instructions and data may be stored in a long-term memory, for example, a non-volatile magnetic, optical, or electronic memory storage device, which is not separately shown. Either or both of the RAM or the storage device may comprise a non-transitory computer-readable medium holding program instructions, that when executed by the processor 1508, cause the apparatus 1502 to perform a method or operations as described herein. Program instructions may be written in any suitable high-level language, for example, C, C++, C#, or Java™, and compiled to produce machine-language code for execution by the processor. Program instructions may be grouped into functional modules, to facilitate coding efficiency and comprehensibility. It should be appreciated that such modules, even if discernable as divisions or grouping in source code, are not necessarily distinguishable as separate code blocks in machine-level coding. Code bundles directed toward a specific type of function may be considered to comprise a module, regardless of whether or not machine code on the bundle can be executed independently of other machine code. In other words, the modules may be high-level modules only.

The processor 1508 may optionally receive a user identifier and store the user identifier in the memory device 1506. A user identifier may include or be associated with user biometric data, that may be collected by a biometric sensor or camera included in the assembly 1502 or in a connected or communicatively coupled ancillary device 1538, such as, for example, a smart phone executing a vaporizer interface application. The processor 1508 may generate or receive data indicating a quantity of the vaporizable material 1530, 1532 consumed by the vaporizer 1520 in a defined period of time, or a record of disposition of one or more of the materials, or a scheme for disposition of the materials, and save the data in the memory device 1506. The processor 1508 and other electronic components may be powered by a suitable battery 1510, as known in the art, or other power source.

The assembly 1502 may include a sensor 1516, or multiple sensors 1516, 1518, to provide measurement feedback to the processor. For example, a sensor 1516 may be positioned downstream of the vaporizer, and the processor may derive the data used for controlling vaporization rate at least in part by interpreting a signal from the sensor correlated to a quantity of vapor emitted by the vaporizer. For further example, a sensor 1518 positioned upstream of the vaporizer, and the processor may derive the data at least in part by interpreting a signal from the sensor correlated to an amount of the vaporizable material remaining in the container, or to an amount of the vaporizable material passed from the container to the vaporizer, or both. "Downstream" and "upstream" relate to the direction of air flow or air/vapor mixture flow through the apparatus 1502, as illustrated by discharge arrow 1534 and inlet 1536. Suction applied at a tip draws inlet air 1536 through the vaporizer 1520, discharging a vapor/air mixture 1535 at the tip. Sensors 1516, 1518 may include, for example, optical sensors, temperature sensors, motion sensors, flow speed sensors, microphones or other sensing devices.

In related aspects, the assembly may include a transmitter port 1514 coupled to the processor. The memory 1506 may hold a designated network address, and the processor 1508 may provide data indicating the quantity of the vaporizable material consumed by the vaporizer and/or disposition of the vaporizable materials 1530, 1532 to the designated network address in association with the user identifier, via the transmitter port 1514.

An ancillary device, such as a smartphone 1538, tablet computer, or similar device, may be coupled to the transmitter port 1514 via a wired or wireless coupling. For example, the apparatus 1502 may include a serial port, for example a USB port, coupled to receiver and transmitter inputs to the processor 1508. In the alternative, or in addition, a wireless port (not shown) using Wifi (IEEE 802.11), Bluetooth, infrared, TCP/IP, Ethernet, UDP, WAP, Bluetooth, Near Field Communication (NFC), Z-wave, LPWAP, Telnet, HTTP, HTTPs, GSM, CDMA, LTE or other communication protocol may be coupled to the processor 1508. The ancillary device 1538 may be coupled to the processor 1508 for providing user control input to vaporizer control process operated executing on the processor 1508. User control input may include, for example, selections from a graphical user interface or other input (e.g., textual or directional commands) generated via a touch screen, keyboard, pointing device, microphone, motion sensor, camera, or some combination of these or other input devices, which may be incorporated in the ancillary device 1538. A display 1539 of the ancillary device 1538 may be coupled to the processor 1508, for example via a graphics processing unit (not shown) integrated in the ancillary device 1538. The display 1539 may include, for example, a flat screen color liquid crystal (LCD) display illuminated by light-emitting diodes (LEDs) or other lamps, a projector driven by an LED display or by a digital light processing (DLP) unit, or other digital display device. User interface output driven by the processor 1508 may be provided to the display device 1539 and output as a graphical display to the user. Similarly, an amplifier/speaker or other audio output transducer of the ancillary device 1538 may be coupled to the processor 1508 via an audio processing system. Audio output correlated to the graphical output and generated by the processor 1508 in conjunction with the ancillary device 1538 may be provided to the audio transducer and output as audible sound to the user.

The ancillary device 1538 may be communicatively coupled via an access point 1540 of a wireless telephone network, local area network (LAN) or other coupling to a wide area network (WAN) 1544, for example, the Internet. A server 1542 may be coupled to the WAN 1544 and to a database 1548 or other data store, and communicate with the apparatus 1502 via the WAN and couple device 1539. In alternative embodiments, functions of the ancillary device 1539 may be built directly into the apparatus 1502, if desired.

In related aspects, the processor 1508 may receive a request for replenishing the vaporizable material 1530 in the container 1522 via at least one of the receiver 1512 or a user input port coupled to the processor 1508. For example, the assembly 1502 may include a user input device coupled to the receiver port 1512. The processor 1508 may be configured to send the request to a designated network address stored in the memory device 1506 in association with the user identifier, via the transmitter port 1514. For example, the processor 1508 may send the request to a commerce server 1542, or to a server hosted by a medical or other service provider. Accordingly, the processor 1508 may facilitate a commercial transaction for replenishing the vaporizable material 1530, at least in part by sending a payment authorization associated with the replenishment request via the transmitter port 1514, by receiving a proof-of-payment certificate via the receiver port 1512, or by some combination of these or other operations.

In another aspect, an inlet port may be coupled to the container 1522 configured to admit the vaporizable material 1530 or a non-vaporizable material into the container 1522. Accordingly, the processor may be configured to provide one of the payment authorization or the proof-of-payment certificate to a device that dispenses the vaporizable material or the non-vaporizable material via such port.

The described technology may enable users to remotely access and authorize activation of a vaporization device, for example, an electronic cigarette or the like, in one or more transactions with a supplier or medical provider. Beyond this, a user or third party may control disposition of materials in the vaporizer 1502. Such dispositions may include, for example, transitioning between enablement of on-demand vaporization of the vaporizable material and disablement of such vaporization, blending the vaporizable material with another vaporizable material, combining the vaporizable material with the non-vaporizable material, transforming the vaporizable material or the non-vaporizable material to a different phase, chemically transforming the vaporizable material or the non-vaporizable material, replenishing the vaporizable material or the non-vaporizable material in the electronic vaporizer, depleting the vaporizable material in the electronic vaporizer without vaporizing it, or depleting the non-vaporizable material in the electronic vaporizer without dispensing it.

The transactions and/or dispositions may be based at least in part on measurements of vaporizable material or non-vaporizable material consumed at a vaporization device identified with a specific user. The transactions and/or dispositions may enable a user to replenish supply of a vaporizable material or non-vaporizable material, unlock permission to vaporize the material at a vaporizing device, or unlock permission to dispense a non-vaporizable material. This may be useful for ordinary commercial transaction, enforcing medically-based dose regimens, or other applications. Potency of the resulting vapor may be controlled by selectively vaporizing contents of two or more containers 1522, 1524 to avoid accidental over consumption of an active substance such as nicotine, caffeine, vitamin B, cannabinoids, or any other non-inert substance. Likewise, potency of an ingestible or inhalable non-vaporized output may be controlled by blending two or more containers holding non-vaporizable materials. Accordingly, the user may continue to enjoy use of the vaporizer 1502 for as long as desired, without experiencing any risk or unpleasant side effects of consuming an excess of active substances.

Figure 16:
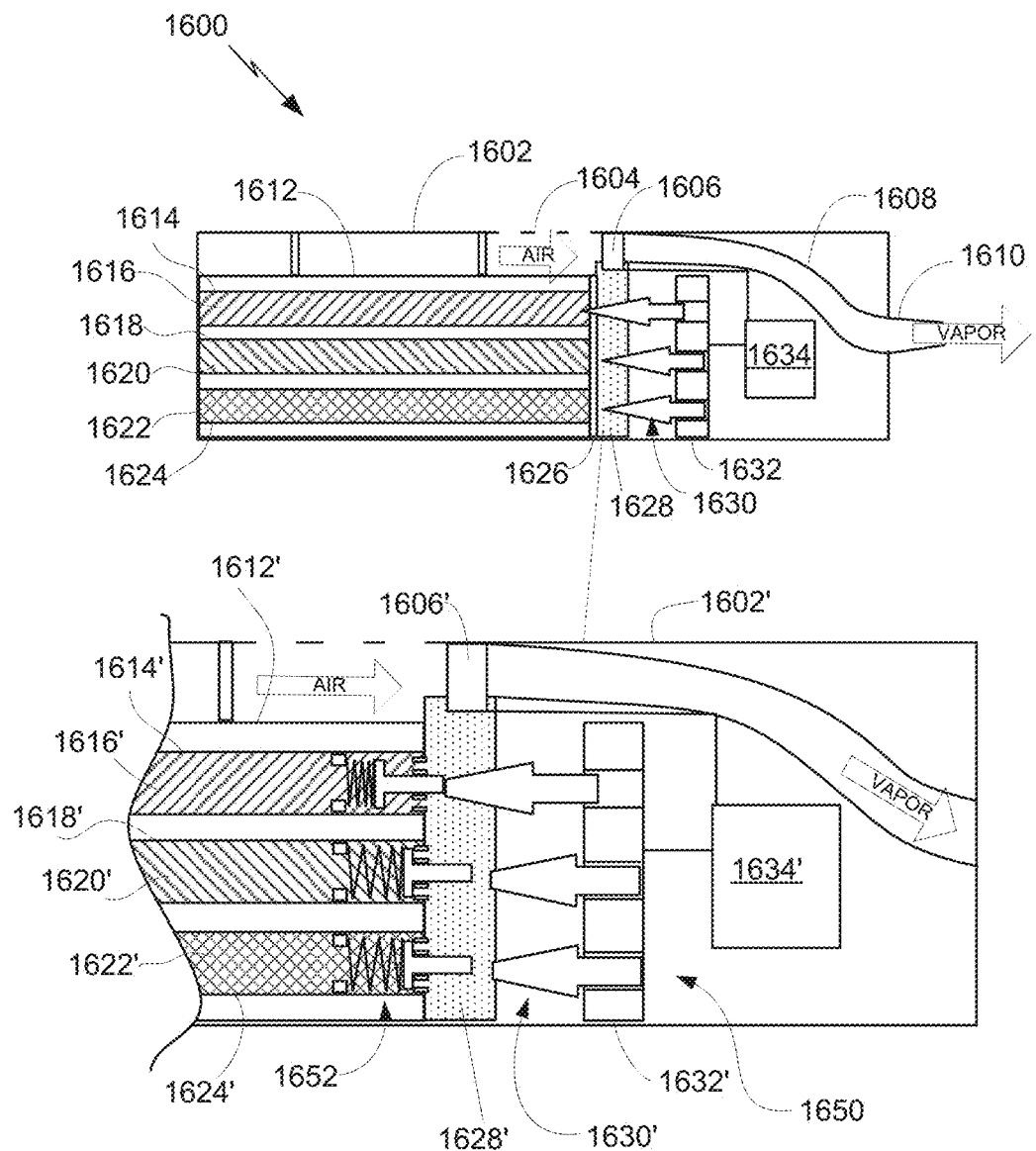
FIG. 16 illustrates an example vaporizer apparatus.

Referring to FIG. 16, another example of a vaporizing apparatus 1600 including component for handling or disposing of a vaporizable material is shown. The apparatus 1600 include an outer housing or envelope 1602 substantially enclosing its interior components, which may be configured to resemble any desired article. In embodiments, the housing 1602 may be configured to resemble a traditional smoking or vaping article (e.g., a cigarette, cigar, cylindrical vaporizer, or hookah), or some other kind of article that is not traditionally use for smoking or vaping (e.g., a mobile phone, a pen, a pencil, a key chain ornament, a piece of fruit, a piece of candy, etc.). The apparatus 1600 may include a multi-chambered cartridge 1612 inserted into a receptacle of the housing. The cartridge 1612 may include multiple containers or receptacles 1614, 1618, 1624 each holding one of different vaporizable materials 1616, 1620, 1622. Prior to first use, a dispensing end of the cartridge 1612 may be sealed by a thin polymer membrane, composite, or foil barrier 1626 that prevents disposition of the materials 1616, 1620, 1622 into a vaporizing inlet compartment 1628. Once depleted, or prior to depletion, the cartridge 1612 may be removed and replaced with a different cartridge containing the materials 1616, 1620, 1622, or different materials. A depleted cartridge may be disposed of, or refilled by a user or commercial supplier.

The vaporizing inlet compartment 1628 is operatively coupled to a vaporizing component 1606, such that material introduced into the compartment 1628 is fed into the vaporizing component 1606. The vaporizing component may be controlled by the electrical circuit 1634 as described elsewhere herein. Likewise, the circuit 1634 may include various components shown and described elsewhere herein, for example, a processor, memory, one or more sensors, input/output ports, electrical leads and connectors, and ancillary components. In operation, one or more of the vaporizable materials 1616, 1620, 1622 may be supplied to the vaporizing component 1606 via the inlet compartment 1628. The vaporizing component 1606 under control of the circuit 1634 may convert the supplied material(s) and air supplied via an inlet 1604 to a vapor supplied to a vapor conduit 1608. The vapor may be withdrawn via a mouthpiece or discharge port 1610 by application of suction, or blown out under positive pressure. As noted herein above, in some embodiments, application of suction may be detected using a sensor and used to activate the vaporizer 1606. The electrical circuit 1634 may be configured for communicating via a communication network using at least one protocol selected from: Wifi, TCP/IP, Ethernet, UDP, WAP, Bluetooth, Near Field Communication (NFC), Z-wave, LPWAP, Telnet, HTTP, HTTPs, GSM, CDMA or LTE, for control or data sharing.

A disposition control mechanism 1632 may be positioned in the housing 1602 adjacent to the barrier 1626. In the illustrated embodiment, the disposition control mechanism comprises an array of linear actuators 1630 each tipped with a piercing tip configured for piercing the membrane 1626. The uppermost one of the actuators 1630 is shown in an activated position piercing the membrane over the outlet of the container 1614 only, thereby allowing ingress of the material 1616 into the inlet compartment 1628. The other two actuators are depicted in a deactivated or retracted position, prior to piercing the membrane 1626. Thus, the containers 1618, 1628 in the illustrated state of the apparatus 1600 remain sealed, and the materials 1620, 1622 are blocked from entry to the vaporization inlet. Actuators 1630 may be impelled using gas or fluid pressure, by electromagnetic force, by a spring or flexing mechanical element, by electrical charge, magnetic force, or any combination of the foregoing.

In the illustrated upper embodiment, the mechanism 1632 and membrane 1626 allow for unlocking access to a sealed material, but not relocking access after the membrane has been punctured. In other embodiments, the membrane and mechanism 1632 may be adapted to permit relocking. For example, an alternative disposition control mechanism 1650, shown in the lower embodiment, may allow for resealing of a material container. A cartridge 1612' may include multiple containers or receptacles 1614', 1618', 1624' each holding one of different vaporizable materials 1616', 1620', 1622'. Before insertion into the vaporizer or after insertion and prior to use, an array of valves or gates 1652 prevents disposition of the materials 1616, 1620, 1622 into a vaporizing inlet compartment 1628. Although depicted as integrated into the cartridge 1612', the valve array 1652 may in alternative embodiments be integrated into the housing 1602' and remain in place when the cartridge 1612' is removed. Once depleted, or prior to depletion, the cartridge 1612' may be removed and replaced with a different cartridge. Advantageously, the integrated valve array 1652 allows the cartridge to be conveniently removed prior to depletion of its contained materials, without spillage.

The vaporizing inlet compartment 1628' is operatively coupled to a vaporizing component 1606' as described above for the upper embodiment. The vaporizing component 1606' may be controlled by the electrical circuit 1634' as also described above. The disposition control mechanism 1650 may be positioned in the housing 1602' adjacent to the valve array 1652. In the illustrated embodiment, the disposition control mechanism comprises an array of linear actuators 1630' each configured for depressing a plunger of the valve array 1652. The uppermost one of the actuators 1630' is shown in an activated position opening the uppermost valve of the array 1652, thereby allowing ingress of the material 1616' into the inlet compartment 1628'. The other two actuators are depicted in a deactivated or retracted position, with the corresponding lower two valves of the array 1652 closed. Thus, the containers 1618', 1628' in the illustrated state of the apparatus remain sealed, and the materials 1620', 1622' are blocked from entry to the vaporization inlet. Actuators 1630' may be impelled as described above. Individual valves of the array 1652 may comprise components such as, for example, a slide bearing, a plunger positioned for sliding in the bearing, an outlet, a seal configured to contact the plunger and seal the outlet under the force of a spring, and ancillary components. Other types of valves or gates may also be suitable, such as for example ball valves or gate valves. In alternative components, the valve array may be supplemented or replaced by a pump array.

It should be appreciated that in the apparatuses described herein, components for holding, controlling disposition of, or dispensing vaporizable materials may likewise be applied for holding, controlling disposition of, or dispensing non-vaporizable materials, with the exception of course of the vaporizing components. Instead of a vaporizing component, a nebulizer or other dispensing component may be used to convert non-vaporizable materials into an inhalable or ingestible form. The electronic vaporizer may exclude any non-vaporizable material (i.e., may hold only one or more vaporizable materials and not any non-vaporizable materials). Conversely, the electronic vaporizer may exclude any vaporizable material (i.e., may hold only one or more non-vaporizable materials and not any vaporizable materials). In the former case, the vaporizer may be used temporarily or permanently as a dispenser of exclusively vaporizable materials in an ingestible or inhalable form. In the latter case, the vaporizer may be used temporarily or permanently as a dispenser of exclusively non-vaporizable materials in an ingestible or inhalable form. In other cases, the vaporizer may be used temporarily or permanently as a dispenser of both vaporizable and non-vaporizable materials in an ingestible or inhalable form.

Figure 17:
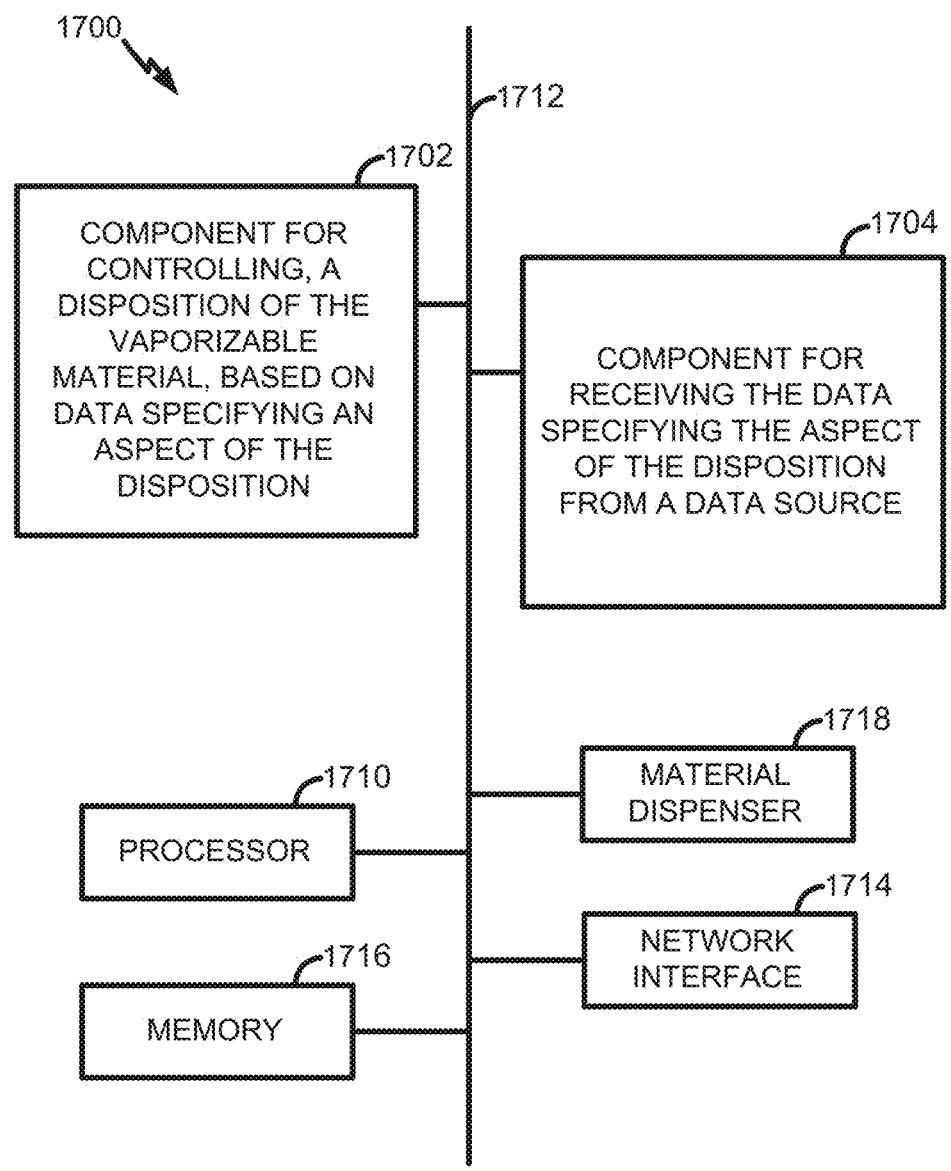
FIG. 17 illustrates an example vaporizer apparatus.

FIG. 17 is a block diagram illustrating components of an apparatus or system 1700 for handling or disposing of a vaporizable material in an electronic vaporizer, in accord with the foregoing examples. The apparatus or system 1700 may include additional or more detailed components as described herein. For example, the processor 1710 and memory 1716 may contain an instantiation of a controller for a vaporizer or nebulizer as described herein, and other ancillary components. As depicted, the apparatus or system 1700 may include functional blocks that can represent functions implemented by a processor, software, or combination thereof (e.g., firmware).

As illustrated in FIG. 17, the apparatus or system 1700 may comprise an electrical component 1702 for controlling a rate at which a vaporizer vaporizes a vaporizable material, based on variable data specifying the rate. The component 1702 may be, or may include, a means for controlling a disposition of the vaporizable material, based on data specifying an aspect of the disposition. Said means may include the processor 1710 coupled to the memory 1716, and to the network interface 1714 and fluid dispenser (e.g., a heat-driven vaporizer), the processor executing an algorithm based on program instructions stored in the memory. Such algorithm may include a sequence of more detailed operations, for example, as described in connection with the methods disclosed herein.

The apparatus or system 1700 may further comprise an electrical component 1704 for receiving or obtaining data specifying the aspect of the disposition from a data source. In an aspect, the data source may be external to the electronic vaporizer. In an alternative, or in addition, the data source may be internal, for example, an internal memory device. "An aspect of the disposition" may include any one or more of control parameters for controlling a disposition control mechanism as described herein. The component 1704 may be, or may include, a means for receiving or obtaining the aspect of the disposition from a data source. Said means may include the processor 1710 coupled to the memory 1716, and to the network interface 1714, the processor executing an algorithm based on program instructions stored in the memory. Such algorithm may include a sequence of more detailed operations, for example, retrieving a network address from the memory 1716, sending a query requesting the data to a network address, and receiving a transmission including the requested data from a server at the network address. In the alternative, or in addition, such algorithm may include receiving a data broadcast or unicast message including the data from the server or from a coupled ancillary device, without the broadcast or unicast message being preceded by a data request. For example, a server may transmit vaporization control parameters periodically or automatically as part of a device initiation process.

The apparatus 1700 may include a processor module 1710 having at least one processor, in the case of the apparatus 1700 configured as a controller configured to operate a fluid dispenser 1718 and other components of the apparatus. The processor 1710, in such case, may be in operative communication with the memory 1716, interface 1714 or dispenser/vaporizer 1718 via a bus 1712 or similar communication coupling. The processor 1710 may effect initiation and scheduling of the processes or functions performed by electrical components 1702-1704.

In related aspects, the apparatus 1700 may include a network interface module operable for communicating with a server over a computer network. The apparatus may include a controllable dispenser 1718 for a vaporizable material, for example, a heat-driven vaporizer for which vaporization rate is correlated to power supplied, or a disposition control mechanism for which dispensing of a vaporizing material is proportional to a control setting, or a disposable barrier such as a foil or membrane cover that can be punctured to allow fluid to flow. In further related aspects, the apparatus 1700 may optionally include a module for storing information, such as, for example, a memory device/module 1716. The computer readable medium or the memory module 1716 may be operatively coupled to the other components of the apparatus 1700 via the bus 1712 or the like. The memory module 1716 may be adapted to store computer readable instructions and data for enabling the processes and behavior of the modules 1702-1704, and subcomponents thereof, or of the methods disclosed herein. The memory module 1716 may retain instructions for executing functions associated with the modules 1702-1704. While shown as being external to the memory 1716, it is to be understood that the modules 1702-1704 can exist within the memory 1716.

In view the foregoing, and by way of additional example, FIG. 18, FIG. 19, and FIG. 20 show aspects of a method or methods for handling or disposing of a vaporizable material or a non-vaporizable material in an electronic vaporizer, alone or in combination with other elements of the systems and apparatuses disclosed, or their equivalents. Referring to FIG. 18, the method 1800 may include, at 1810, activating electronic vaporizer that includes a container for holding a vaporizable material, a vaporizer coupled to the container for vaporizing the vaporizable material, and a processor. For example, a motion sensor may detect movement after a period of stillness, and send an activation interrupt to a sleeping processor, which in response to the interrupt may power up the control circuitry of the vaporizer and begin an initialization sequence.

The method 1800 may further include, at 1820, controlling, by the processor, a disposition of the vaporizable material, based on data specifying an aspect of the disposition. For example, the data may specify an identifier for a vaporizable material or associated control mechanism that is to be activate or deactivated, and any associated control parameters for the mechanism. The physical result of the disposition may depend on the structure of the disposition control mechanisms and the components to which the control mechanism is coupled. Various examples have been provided above, and additional examples are provided below.

The method 1800 may further include, at 1830, receiving the data specifying the disposition from a data source external to the electronic vaporizer. For example, the processor may at any time prior to the operation 1820, receive data from a connected smartphone or the like that sets a target dosing profile for one or more identified users. In the alternative, or in addition, the processor may receive data used in controlling vaporization during or after a control operation 1820. In an alternative, or in addition, the data source may be internal to the vaporizer, for example, may be an internal memory device.

The method 1800 may include any one or more of additional operations 1900, shown in FIG. 19, in any operable order. Each of these additional operations is not necessarily performed in every embodiment of the method, and the presence of any one of the operations 1900 does not necessarily require that any other of these additional operations also be performed. The operations 1900 may be performed using any suitable apparatus as described herein, or their equivalents.

Referring to FIG. 19 showing additional operations 1900, the method 1800 may further include, at 1910, transitioning between enablement of on-demand vaporization of the vaporizable material and disablement of such vaporization. For example, a vaporizable material may be locked, preventing it from being vaporized for a period of time. After a period of time in a locked state, access may be unlocked, enabling vaporization of the material again. Likewise, a non-vaporizable material may be locked or unlocked.

The method 1800 may include, at 1920, combining the vaporizable material with another vaporizable material. For example, two or more vaporizable materials may be dispensed together into a blending chamber or duct, and provided to a vaporizer. In an alternative, or in addition, two or more vaporizable materials may be provided to different vaporizers, vaporized separately, and combined downstream of the vaporizers prior to exiting a mouthpiece or other discharge port.

In addition, or in the alternative, the method 1800 may include, at 1930, combining the vaporizable material with a non-vaporizable material. For example, a vaporizable material may be vaporized to produce a vapor, and a liquid, gas, or solid particulate introduced into the vapor prior to dispensing the vapor from a mouthpiece or the like. Introduction of a liquid, gas or solid particulate material may be useful, for example, to enhance flavor of a vapor by providing a greater concentration of active ingredient than can be provided in vapor form, to supply a material (e.g., a flavor, nutrient, vitamin, herbal essence, chemical, inert carrier, pharmaceutical or medicine) that would be altered or destroyed by the available vaporization process, to supply a material that would damage or shorten the life of the vaporization element, to supply a material that cannot be vaporized by the vaporization element, or to obtain a synergistic effect.

In the alternative, or in addition, the method 1800 may include, at 1940 at least one of transforming the vaporizable material to a different phase or chemically transforming the vaporizable material. For example, the vaporizing apparatus may melt or sublime a solid material before providing to a vaporizing element, or evaporate a liquid material. In the alternative, or in addition, the vaporizing apparatus may expose the vaporizable material to another element that causes a chemical change, for example, an oxidation or reduction reaction, or a combination of reactants to provide a product. In addition, or in the alternative, these transformations may be performed on non-vaporizable materials.

In the alternative, or in addition, the method 1800 may include, at 1950, at least one of replenishing the vaporizable material in the electronic vaporizer or depleting the vaporizable material in the electronic vaporizer without vaporizing it. For example, the vaporizing apparatus may refill or recharge a reservoir from an external source, or from another reservoir internal to the electronic vaporizer. In the alternative, or in addition, the vaporizing apparatus may empty a reservoir to an external sink, or from a vaporizing reservoir to another reservoir (e.g., a storage reservoir) internal to the electronic vaporizer. For example, a user may partially or entirely deplete a storage reservoir to supply a material to a different vaporizing device, or to make room for addition of a new material. In addition, or in the alternative, replenishing or depleting may be similarly performed on non-vaporizable materials.

An electronic vapor device is disclosed comprising a first container for storing a vaporizable material, a vaporizer component coupled to the first container, configured for vaporizing the vaporizable material, a processor coupled to the vaporizer component, configured to control the vaporizer component in response to a disposition signal, and a network access device, coupled to the processor, configured for receiving the disposition signal from a remote server.

The disposition signal can comprise one or more of, a command to vaporize the vaporizable material, a command to disable the vaporizer component, a command to enable the vaporizer component, a command to place the vaporizer component in an on-demand state, a command to mix the vaporizable material with another vaporizable material, a command to mix the vaporizable material with a non-vaporizable material, a command to replenish the vaporizable material, a command to deplete the vaporizable material without vaporizing the vaporizable material.

The network access device can communicate via one or more of, Wi-Fi, TCP/IP, Ethernet, UDP, WAP, Bluetooth, Near Field Communication (NFC), Z-wave, LPWAP, Telnet, HTTP, HTTPs, GSM, CDMA, or LTE.

The electronic vapor device can further comprise a disposition control mechanism operatively interposed between the vaporizer component and the first container, configured to execute a function based on the disposition signal. The disposition control mechanism can comprise at least one of: a valve, a membrane, a foil barrier, a stationary wick, a movable wick, a bubble jet, a piezoelectric pump, a microfluidic pump, a mechanical pump, or a heater. The disposition signal can comprise a command to replenish the vaporizable material and wherein the disposition control mechanism can be configured to replenish the first container from a reservoir internal to the electronic vapor device.

The electronic vapor device can further comprise a memory device coupled to the processor, wherein the processor can be configured to receive a user identifier and to store the user identifier in the memory device. The processor can be further configured to generate data indicating a quantity of the vaporizable material consumed by the vaporizer component in a defined period of time, and to save the data in the memory device.

The electronic vapor device can further comprise a sensor positioned downstream of the vaporizer component, wherein the processor can be further configured to generate the data at least in part by interpreting a signal from the sensor correlated to a quantity of vapor emitted by the vaporizer component. The electronic vapor device can further comprise a sensor positioned upstream of the vaporizer component, wherein the processor can be further configured to generate the data at least in part by interpreting a signal from the sensor correlated to at least one of: an amount of the vaporizable material remaining in the first container, or an amount of the vaporizable material passed from the first container to the vaporizer component.

The processor can be further configured to transmit the data in association with the user identifier to the remote server via the network access device. The electronic vapor device can further comprise an input device, coupled to the processor, configured to receive a request for replenishing the vaporizable material. The processor can be further configured to transmit the request in association with the user identifier to the remote server via the network access device. The processor can be further configured to facilitate a commercial transaction for replenishing the vaporizable material, at least in part by one of more of: transmitting a payment authorization associated with the request via the network access device to the remote server and receiving a proof-of-payment certificate via the network access device from the remote server.

The electronic vapor device can further comprise a second container for storing a non-vaporizable material, a dispenser coupled to the second container, configured for dispensing the non-vaporizable material, and wherein the processor can be coupled to the dispenser and configured to control the dispenser in response to the disposition signal. The disposition signal can comprise one or more of, a command to dispense the non-vaporizable material, a command to disable the dispenser, a command to enable the dispenser, a command to place the dispenser in an on-demand state, a command to mix the non-vaporizable material with another non-vaporizable material, a command to mix the vaporizable material with the non-vaporizable material, a command to replenish the non-vaporizable material, a command to deplete the non-vaporizable material without dispensing the non-vaporizable material.

Referring to FIG. 20, a method 2000 is disclosed comprising receiving, by an electronic vapor device, a disposition signal from a remote server at 2010. The method 2000 can comprise determining, by the electronic vapor device, a command based on the disposition signal at 2020. The method 2000 can comprise executing the command, by the electronic vapor device, wherein executing the command affects a disposition of a vaporizable material at 2030.

The disposition signal can be received via one or more of, Wi-Fi, TCP/IP, Ethernet, UDP, WAP, Bluetooth, Near Field Communication (NFC), Z-wave, LPWAP, Telnet, HTTP, HTTPs, GSM, CDMA, or LTE. The command can comprise one or more of a command to vaporize the vaporizable material, a command to disable the vaporizer component, a command to enable the vaporizer component, a command to place the vaporizer component in an on-demand state, a command to mix the vaporizable material with another vaporizable material, a command to mix the vaporizable material with a non-vaporizable material, a command to replenish the vaporizable material, a command to deplete the vaporizable material without vaporizing the vaporizable material.

Executing the command can comprise activating a disposition control mechanism operatively interposed between a vaporizer component and a container of the electronic vapor device. The disposition control mechanism can comprise at least one of: a valve, a membrane, a foil barrier, a stationary wick, a movable wick, a bubble jet, a piezoelectric pump, a microfluidic pump, a mechanical pump, or a heater.

The method 2000 can further comprise receiving a user identifier and storing the user identifier in a memory component.

The method 2000 can further comprise receiving a request for replenishing the vaporizable material. The method 2000 can further comprise transmitting the request in association with the user identifier to the remote server. The method 2000 can further comprise facilitating a commercial transaction for replenishing the vaporizable material, at least in part by one of more of: transmitting a payment authorization associated with the request the remote server and receiving a proof-of-payment certificate from the remote server. The method 2000 can further comprise receiving a second disposition signal from the remote server, determining a command to replenish the vaporizable material based on the second disposition signal, and replenishing the container from a reservoir internal to the electronic vapor device.

Executing the command, by the electronic vapor device, wherein executing the command affects a disposition of a vaporizable material can comprise affecting a disposition of a non-vaporizable material. The disposition signal can comprise one or more of, a command to dispense the non-vaporizable material, a command to disable the dispenser, a command to enable the dispenser, a command to place the dispenser in an on-demand state, a command to mix the non-vaporizable material with another non-vaporizable material, a command to mix the vaporizable material with the non-vaporizable material, a command to replenish the non-vaporizable material, a command to deplete the non-vaporizable material without dispensing the non-vaporizable material.

The methods disclosed may include any one or more of additional operations of any other method in any operable order. Each of these additional operations is not necessarily performed in every embodiment of the method, and the presence of any one operation does not necessarily require that any other additional operations also be performed.

In view of the exemplary systems described supra, methodologies that can be implemented in accordance with the disclosed subject matter have been described with reference to several flow diagrams. While for purposes of simplicity of explanation, the methodologies are shown and described as a series of blocks, it is to be understood and appreciated that the claimed subject matter is not limited by the order of the blocks, as some blocks may occur in different orders and/or concurrently with other blocks from what is depicted and described herein. Moreover, not all illustrated blocks can be required to implement the methodologies described herein. Additionally, it should be further appreciated that the methodologies disclosed herein are capable of being stored on an article of manufacture to facilitate transporting and transferring such methodologies to computers.

Those of skill would further appreciate that the various illustrative logical blocks, modules, circuits, and algorithm steps described in connection with the aspects disclosed herein can be implemented as electronic hardware, computer software, or combinations of both. To clearly illustrate this interchangeability of hardware and software, various illustrative components, blocks, modules, circuits, and steps have been described above generally in terms of their functionality. Whether such functionality is implemented as hardware or software depends upon the particular application and design constraints imposed on the overall system. Skilled artisans may implement the described functionality in varying ways for each particular application, but such implementation decisions should not be interpreted as causing a departure from the scope of the present disclosure.

As used in this application, the terms "component," "module," "system," and the like are intended to refer to a computer-related entity, either hardware, a combination of hardware and software, software, or software in execution. For example, a component can be, but is not limited to being, a process running on a processor, a processor, an object, an executable, a thread of execution, a program, and/or a computer. By way of illustration, both an application running on a server and the server can be a component. One or more components may reside within a process and/or thread of execution and a component can be localized on one computer and/or distributed between two or more computers.

As used herein, a "vapor" includes mixtures of a carrier gas or gaseous mixture (for example, air) with any one or more of a dissolved gas, suspended solid particles, or suspended liquid droplets, wherein a substantial fraction of the particles or droplets if present are characterized by an average diameter of not greater than three microns. As used herein, an "aerosol" has the same meaning as "vapor," except for requiring the presence of at least one of particles or droplets. A substantial fraction means 10% or greater, however, it should be appreciated that higher fractions of small (<3 micron) particles or droplets can be desirable, up to and including 100%. It should further be appreciated that, to simulate smoke, average particle or droplet size can be less than three microns, for example, can be less than one micron with particles or droplets distributed in the range of 0.01 to 1 micron. A vaporizer may include any device or assembly that produces a vapor or aerosol from a carrier gas or gaseous mixture and at least one vaporizable material. An aerosolizer is a species of vaporizer, and as such is included in the meaning of vaporizer as used herein, except where specifically disclaimed.

Various aspects presented in terms of systems can comprise a number of components, modules, and the like. It is to be understood and appreciated that the various systems may include additional components, modules, etc. and/or may not include all of the components, modules, etc. discussed in connection with the figures. A combination of these approaches can also be used.

In addition, the various illustrative logical blocks, modules, and circuits described in connection with certain aspects disclosed herein can be implemented or performed with a general purpose processor, a digital signal processor (DSP), an application specific integrated circuit (ASIC), a field programmable gate array (FPGA) or other programmable logic device, discrete gate or transistor logic, discrete hardware components, or any combination thereof designed to perform the functions described herein. A general purpose processor can be a microprocessor, but in the alternative, the processor can be any conventional processor, controller, microcontroller, system-on-a-chip, or state machine. A processor may also be implemented as a combination of computing devices, e.g., a combination of a DSP and a microprocessor, a plurality of microprocessors, one or more microprocessors in conjunction with a DSP core, or any other such configuration.

Operational aspects disclosed herein can be embodied directly in hardware, in a software module executed by a processor, or in a combination of the two. A software module may reside in RAM memory, flash memory, ROM memory, EPROM memory, EEPROM memory, registers, hard disk, a removable disk, a CD-ROM, a DVD disk, or any other form of storage medium known in the art. An exemplary storage medium is coupled to the processor such the processor can read information from, and write information to, the storage medium. In the alternative, the storage medium can be integral to the processor. The processor and the storage medium may reside in an ASIC or may reside as discrete components in another device.

Furthermore, the one or more versions can be implemented as a method, apparatus, or article of manufacture using standard programming and/or engineering techniques to produce software, firmware, hardware, or any combination thereof to control a computer to implement the disclosed aspects. Non-transitory computer readable media can include but are not limited to magnetic storage devices (e.g., hard disk, floppy disk, magnetic strips . . . ), optical disks (e.g., compact disk (CD), digital versatile disk (DVD) . . . ), smart cards, and flash memory devices (e.g., card, stick). Those skilled in the art will recognize many modifications can be made to this configuration without departing from the scope of the disclosed aspects.

The previous description of the disclosed aspects is provided to enable any person skilled in the art to make or use the present disclosure. Various modifications to these aspects will be readily apparent to those skilled in the art, and the generic principles defined herein can be applied to other embodiments without departing from the spirit or scope of the disclosure. Thus, the present disclosure is not intended to be limited to the embodiments shown herein but is to be accorded the widest scope consistent with the principles and novel features disclosed herein.

Unless otherwise expressly stated, it is in no way intended that any method set forth herein be construed as requiring that its steps be performed in a specific order. Accordingly, where a method claim does not actually recite an order to be followed by its steps or it is not otherwise specifically stated in the claims or descriptions that the steps are to be limited to a specific order, it is in no way intended that an order be inferred, in any respect. This holds for any possible non-express basis for interpretation, including: matters of logic with respect to arrangement of steps or operational flow; plain meaning derived from grammatical organization or punctuation; the number or type of embodiments described in the specification.

It will be apparent to those skilled in the art that various modifications and variations can be made without departing from the scope or spirit. Other embodiments will be apparent to those skilled in the art from consideration of the specification and practice disclosed herein. It is intended that the specification and examples be considered as exemplary only, with a true scope and spirit being indicated by the following claims.

The invention claimed is:

1. An electronic vapor device comprising:
   a processor operable for controlling the electronic vaporizer device;
   a first container for storing a vaporizable material;
   a vaporizer component operatively coupled to the processor and controlled in part by the processor, wherein the vaporizer component is in fluid communication with the first container for receiving at least a portion of the vaporizable material therefrom, wherein the vaporizer component is operable to vaporize the vaporizable material received therein;
   a network access device operatively coupled to the processor and controlled by in part by the processor, wherein the network access device is operable to receive at least one disposition signal from a remote server;
   a disposition control mechanism operatively coupled to the processor and controlled in part by the processor, wherein the disposition control mechanism is operatively interposed between the vaporizer component and the first container, wherein the disposition control mechanism is operable to execute an operation in response to the at least one received disposition signal, wherein the disposition control mechanism comprises at least one of: a valve, a membrane, a foil barrier, a stationary wick, a movable wick, a bubble jet, a piezoelectric pump, a microfluidic pump, a mechanical pump, a heater, and combinations thereof; and
   wherein the at least one received disposition signal comprises at least one command to replenish the vaporizable material stored in the first container;
   wherein the disposition control mechanism is operable to replenish the first container from a reservoir that is internal to the electronic vapor device in response to the at least one received disposition signal.

2. The electronic vapor device of claim 1, wherein the at least one received disposition signal further comprises at least one of: a command to vaporize the vaporizable material, a command to disable the vaporizer component, a command to enable the vaporizer component, a command to place the vaporizer component in an on-demand state, a command to mix the vaporizable material with one or more non-vaporizable materials, a command to deplete the vaporizable material without vaporizing the vaporizable material, and combinations thereof.

3. The electronic vapor device of claim 1, wherein the network access device is configured to communicate via at least one of: Wi-Fi, TCP/IP, Ethernet, UDP, WAP, Bluetooth, Near Field Communication (NRC), Z-wave, LPWAP, Telnet, HTTP, HTTPS, GSM, CDMA, LTE, and combinations thereof.

4. The electronic vapor device of claim 1, further comprising a memory device coupled to the processor, wherein the processor is operable to receive user identification data from at least one associated user and to store the user identification data in the memory device.

5. The electronic vapor device of claim 4, wherein the processor is further operable to generate vaporization data indicating a quantity of the vaporizable material consumed by the vaporizer component in a defined period of time, and to save the vaporization data in the memory device.

6. The electronic vapor device of claim 5, further comprising: a sensor positioned downstream of the vaporizer component, wherein the sensor is operable determine a quantity of vapor emitted by the vaporizer component and generate at least one vapor emission signal.

7. The electronic vapor device of claim 6, wherein the vaporization data indicating a quantity of vaporizable material consumed is based at least in part on the at least one vapor emission signal.

8. The electronic vapor device of claim 4, wherein the processor is further operable to transmit the user identification data associated with at least one user to the remote server via the network access device.

9. The electronic vapor device of claim 4, wherein the processor is further operable to associate vaporization data with at least one associated user and transmit at least a portion of the generated vaporization data associated with at least one user to the remote server via the network access device.

10. The electronic vapor device of claim 4, further comprising: an input/output device operatively coupled to the processor and controlled in part by the processor, wherein the input/output device is operable to receive at least one request to replenish the vaporizable material.

11. The electronic vapor device of claim 10, wherein the processor is further operable to associate the at least one request to replenish the vaporizable material with at least one associated user and transmit the at least one request associated with at least one user to the remote server via the network access device.

12. The electronic vapor device of claim 11, wherein the processor is further operable to facilitate a commercial transaction for replenishing the vaporizable material, at least in part, by one or more of: transmitting a payment authorization associated with the at least one request, via the network access device to the remote server; and receiving a proof-of-payment certification via the network access device from the remote server.

13. The electronic vapor device of claim 1, further comprising:
   a second container for storing a non-vaporizable material; and
   a dispenser operatively coupled to the processor and controlled in part by the processor, wherein the dispenser is operatively interposed between the vaporizer component and the second container, wherein the dispenser is operable to execute a second operation in response to a second received disposition signal.

14. The electronic vapor device of claim 13, wherein the at least one received disposition signal may comprise at least one of: a command to dispense the non-vaporizable material, a command to disable the dispenser, a command to enable the dispenser, a command to place the dispenser in an on-demand state, a command to mix the vaporizable material with non-vaporizable material, a command to replenish the non-vaporizable material, a command to deplete the non-vaporizable material without dispensing the non-vaporizable material, and combinations thereof.

15. A method of operating an electronic vapor device, wherein the electronic vapor device comprises (a) a first container for storing a vaporizable material, (b) a vaporizer component in fluid communication with the first container for receiving at least a portion of the vaporizable material therefrom, wherein the vaporizer component is operable to vaporize the vaporizable material received therein, (c) a network access device operable to receive at least one disposition signal from a remote server, and (d) a disposition control mechanism operable to execute an operation in response to at least one received disposition signal, wherein the disposition control mechanism comprises at least one of: a valve, a membrane, a foil barrier, a stationary wick, a movable wick, a bubble jet, a piezoelectric pump, a microfluidic pump, a mechanical pump, a heater, and combinations thereof, the method comprising the steps:
   receiving the least one disposition signal from the remote server, wherein the at least one disposition signal comprises at least one command to replenish the vaporizable material stored in the first container;
   replenishing the first container from a reservoir that is internal to the electronic vapor device in response to the at least one received disposition signal.

16. The method of claim 15, wherein the at least one disposition signal is received via at least one of: Wi-Fi, TCP/IP, Ethernet, UDP, WAP, Bluetooth, Near Field Communication (NRC), Z-wave, LPWAP, Telnet, HTTP, HTTPS, GSM, CDMA, LTE, and combinations thereof.

17. The method of claim 15, wherein the at least one received disposition signal may further comprise at least one of: a command to vaporize the vaporizable material, a command to disable the vaporizer component, a command to enable the vaporizer component, a command to place the vaporizer component in an on-demand state, a command to mix the vaporizable material with non-vaporizable material, a command to deplete the vaporizable material without vaporizing the vaporizable material, and combinations thereof.

18. The method of claim 15, further comprising the steps:
   receiving user identification data from at least one associated user and storing the user identification data in an associated memory device.

19. The method of claim 18, further comprising the steps: generating vaporization data indicating a quantity of the vaporizable material consumed by the vaporizer component in a defined period of time and to saving the generated vaporization data in the associated memory device.

20. The method of claim 19, further comprising the steps: associating vaporization data with at least one associated user and transmitting at least a portion of the vaporization data associated with at least one user to the remote server.

* * * * *